United States Patent
Gaston et al.

(10) Patent No.: US 10,543,187 B2
(45) Date of Patent: *Jan. 28, 2020

(54) COMPOSITIONS AND METHODS FOR STIMULATING VENTILATORY AND/OR RESPIRATORY DRIVE

(71) Applicant: CASE WESTERN RESERVE UNIVERSITY, Cleveland, OH (US)

(72) Inventors: Benjamin Gaston, Cleveland, OH (US); Stephen Lewis, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/139,937

(22) Filed: Sep. 24, 2018

(65) Prior Publication Data

US 2019/0231732 A1     Aug. 1, 2019

Related U.S. Application Data

(63) Continuation of application No. 15/543,524, filed as application No. PCT/US2016/013241 on Jan. 13, 2016, now Pat. No. 10,080,732.

(60) Provisional application No. 62/102,902, filed on Jan. 13, 2015.

(51) Int. Cl.
*A61K 31/225* (2006.01)
*A61K 45/06* (2006.01)
*A61K 9/00* (2006.01)

(52) U.S. Cl.
CPC .......... *A61K 31/225* (2013.01); *A61K 9/0019* (2013.01); *A61K 45/06* (2013.01)

(58) Field of Classification Search
CPC ..... A61K 31/225; A61K 45/06; A61K 9/0019
See application file for complete search history.

(56) References Cited

U.S. PATENT DOCUMENTS

| | | |
|---|---|---|
| 6,242,573 B1 | 6/2001 | Goto et al. |
| 2002/0115723 A1 | 8/2002 | Iwasaki et al. |
| 2013/0131028 A1 | 5/2013 | Snyder et al. |
| 2013/0338225 A1 | 12/2013 | Ward et al. |

FOREIGN PATENT DOCUMENTS

WO     1992/04024 A2     3/1992

OTHER PUBLICATIONS

Mendoza et al. (Respir Physiol Neurobiol. (2013) 189(1): 136-143.

*Primary Examiner* — Shirley V Gembeh
(74) *Attorney, Agent, or Firm* — Tarolli, Sundheim, Covell & Tummino LLP

(57) ABSTRACT

A method of stimulating ventilatory and/or respiratory drive in a subject in need thereof includes administering to the subject a therapeutically effective amount of a composition comprising a cystine ester or a pharmaceutically acceptable salt thereof.

18 Claims, 16 Drawing Sheets

COMPOSITIONS AND METHODS FOR STIMULATING VENTILATORY AND/OR RESPIRATORY DRIVE

RELATED APPLICATION

This application claims priority from U.S. Provisional Application No. 62/102,902, filed Jan. 13, 2015, the subject matter of which is incorporated herein by reference in its entirety.

TECHNICAL FIELD

Embodiments described herein relate to compositions and methods of stimulating ventilatory and/or respiratory drive in a subject in need thereof, and particularly relates to compositions and methods of treating breathing diseases and/or disorders associated with impaired ventilatory and/or respiratory drive.

BACKGROUND

Normal control of breathing is a complex process that involves the body's interpretation and response to chemical stimuli, such as carbon dioxide, pH and oxygen levels in blood, tissues and the brain. Breathing control is also affected by wakefulness (i.e., whether the patient is awake or sleeping). Within the brain medulla there are respiratory control centers that interpret the various signals that affect respiration and issue commands to muscles that perform the work of breathing. Key muscle groups are located in the abdomen, diaphragm, larynx, pharynx and thorax. Sensors located centrally and peripherally provide input to the brain's central respiration control areas that enable response to changing oxygen requirements.

Normal respiratory rhythm is maintained primarily by the body's rapid response to changes in carbon dioxide levels ($CO_2$). Increased $CO_2$ levels signal the body to increase breathing rate and depth resulting in higher oxygen levels and subsequent lower $CO_2$ levels. Conversely, low $CO_2$ levels can result in periods of apnea (no breathing) since the stimulation to breathe is absent. This is what happens when a person hyperventilates. Additionally, low blood oxygen levels stimulate respiratory drive, and this mechanism can become the primary driver in patients with chronically high $PCO_2$ levels.

Impaired ventilatory drive can complicate a broad spectrum of diseases in pulmonary, sleep, and critical care medicine. Patients with various forms of chronic obstructive pulmonary disease (COPD)—among which can be considered late-stage cystic fibrosis (CF)—can have impaired ventilatory responses when treated with oxygen or narcotics. In obstructive sleep apnea (OSA), intermittent hypoxia associated with impaired short- and long-term facilitation of hypoxic ventilatory drive and with loop gain may predispose to perioperative complications and adverse neurocognitive sequelae. A variety of other conditions with components of disordered ventilatory control—ranging from congestive heart failure (CHF) to Arnold-Chiari malformation—can only be managed with mechanical ventilation. Additionally, endotracheally-intubated patients in the critical care setting who require narcotics for pain control can become unmanageable if narcotic use is stopped, but can fail extubation because of respiratory depression if the narcotic is continued. These pulmonary and critical care issues can be all the more challenging in patients with underlying COPD, CF, CHF, OSA and other conditions affecting ventilatory drive.

Few medications are effective as respiratory stimulants. Methylxanthines can be effective in patients with apnea of prematurity, but are often ineffective in older patients. Almitrine can transiently improve ventilatory drive in adults with COPD. However, the administration of almitrine is associated with the development of pulmonary arterial hypertension and peripheral neuropathy; and it does not affect outcome.

Conditions associated with impaired ventilatory drive are common and have a substantial public health impact. For example, large, population-based studies report a prevalence of moderate-severe obstructive sleep apnea of 2-14% of the American population-depending on age and gender—and prevalence may be higher (up to 38% of men) in pulmonary clinic. A significant proportion of patients with OSA have impaired ventilatory drive, particularly those who also have heart failure. There is a large, unmet need for a safe and effective respiratory stimulant in pulmonary and critical care medicine.

Additionally, commonly used narcotic and benzodiazepine medications suppress ventilatory drive. Specifically, they depress the slope of the relationship between $PCO_2$ and minute ventilation. This is a major issue in several important settings. In the operating room and post-anesthesia care setting, patients may have prolonged respiratory depression associated with pain control. This results in prolonged hospitalizations or early, risky discharge and death. In the chronic pain population—in the Veteran's Administration system, for example—death from nocturnal respiratory depression is at epidemic proportions among patients on chronic opiate therapy. Opiate addiction is also at epidemic levels, and hundreds of young people die annually without an effective emergency respiratory stimulant. On the battlefield, medics can have to choose between excruciating pain and risk of death from respiratory depression. In the Intensive Care population, physicians often have to choose between the risk of being on the ventilator for one or more days and the risk of awaking a patient in pain and distress. This is a problem in patients with a baseline blunted $CO_2$ response, such as patients with severe COPD, CF or other obstructive lung disease. Emergency treatment for narcotic-induced respiratory depression is limited largely to the use of narcotic antagonists, such as naloxone, which are effective at reversing the narcotic induced respiratory depression but also reverse the narcotic mediated pain control, exacerbating the original problem. Further, this treatment is specific to narcotics and is ineffective for benzodiazepine or other sedative or anesthetic induced respiratory depression. A respiratory stimulant that overcomes respiratory depression from any source is needed to address these needs.

SUMMARY

Embodiments described herein relate to compositions and methods of stimulating ventilatory and/or respiratory drive in a subject in need thereof, and particularly relates to compositions and methods of treating breathing diseases and/or disorders associated with impaired ventilatory and/or respiratory drive.

In some embodiments, the methods can include stimulating ventilatory and/or respiratory drive in a subject in need thereof by administering to the subject a therapeutically effective amount of a composition comprising a cystine ester or a pharmaceutically acceptable salt thereof. The therapeutically effective amount can be an amount effective to stimulate the ventilatory and/or respiratory drive of the subject, including increasing tidal volume and respiratory frequency. The composition can be administered to the subject systemically by, for example, topical (e.g., inhalation), enteral (e.g., oral), and/or parenteral (e.g., intravenous injection) administration.

In some embodiments, the cystine ester can have the formula:

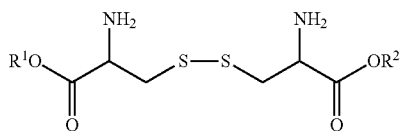

where $R^1$ and $R^2$ are the same or different and are selected from the group consisting of H, unsubstituted or substituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl, and heterocyclyl containing from 5-14 ring atoms, and at least one of $R^1$ and $R^2$ is not a H; or pharmaceutically acceptable salts thereof.

In some embodiments, $R^1$ and $R^2$ are independently H or an unsubstituted or substituted $C_1$-$C_{24}$ alkyl, and at least one of $R^1$ and $R^2$ is not a H. In other embodiments, $R^1$ and $R^2$ are independently selected from the group consisting of H, methyl, ethyl, propyl, and butyl, and at least one of $R^1$ and $R^2$ is not a H.

In other embodiments, the cystine ester can be a cystine dialkyl ester, prodrug thereof, or pharmaceutically acceptable salt thereof. The cystine dialkyl ester can be selected from the group consisting of cystine dimethyl ester, cystine diethyl ester, combinations thereof, and pharmaceutically acceptable salts thereof.

In still other embodiments, the cystine dialkyl ester can be a D-cystine dialkyl ester or pharmaceutically acceptable salt thereof. For example, the D-cystine dialkyl ester can be a D-cystine dimethyl ester, D-cystine diethyl ester, or a pharmaceutically acceptable salt thereof.

In some embodiments, the subject can have or is at increased risk of a breathing disorder, such as respiratory depression, including narcotic, sedative, and/or anesthetic, induced respiratory drive or suppresses ventilatory drive, sleep apnea (central, mixed and obstructive including but not limited to co-existing conditions of heart failure, kidney disease and stroke), sleep-disordered breathing (especially with snoring and arousals), apnea of prematurity, allergies, neurological or neuromuscular diseases (e.g., stroke or amyotrophic lateral sclerosis (ALS)), weakened respiratory muscles, hypoventilation due to stroke, trauma, surgery and/or radiation, obesity-hypoventilation syndrome, primary alveolar hypoventilation syndrome, acquired central hypoventilation syndromes (ACHS), congenital central hypoventilation syndromes (CCHS), chronic bronchitis, Cheyne-Stokes respiration, dyspnea, altitude sickness or acclimatization to high altitude, hypopnea, hypoxia, hypercapnia, cystic fibrosis, chronic obstructive pulmonary disease (COPD), nasal septum deformation, tonsillitis, adenoiditis, and Arnold-Chiari syndrome; and the composition can be administered to the subject to treat the breathing disorder. For example, the composition can be administered to the subject at an amount effective to prevent the need for mechanical ventilation in subjects with acutely impaired ventilatory and/or respiratory drive because of an acute exacerbation of an underlying lung disease or an acute requirement for narcotic analgesia.

In other embodiments, the subject can have or has an increased risk of respiratory depression that is caused, for example, by an anesthetic, a sleeping aid, a sedative, anxiolytic agent, a hypnotic agent, alcohol, and/or a narcotic.

In still other embodiments, the composition can be administered to a subject in combination with at least one additional therapeutic agent that changes normal breathing in a subject. The additional agent can be selected from the group consisting of doxapram and enantiomers thereof, acetazolamide, almitrine, theophylline, caffeine, methylprogesterone and related compounds, sedatives that decrease arousal threshold in sleep disordered breathing patients, sodium oxybate, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, and combinations thereof.

In yet another embodiment, the composition and the agent are separately administered to the subject. In yet another embodiment, the compound and the agent are co-administered to the subject, further wherein the composition and the agent are physically mixed or physically separated when administered to the subject.

In one embodiment, the subject is further administered at least one additional therapeutic agent that changes normal breathing control in the subject. In another embodiment, the additional agent is at least one selected from the group consisting of opioid narcotics, benzodiazepines, sedatives, sleeping aids, hypnotics, propofol, and any combinations thereof.

Figure 7A:
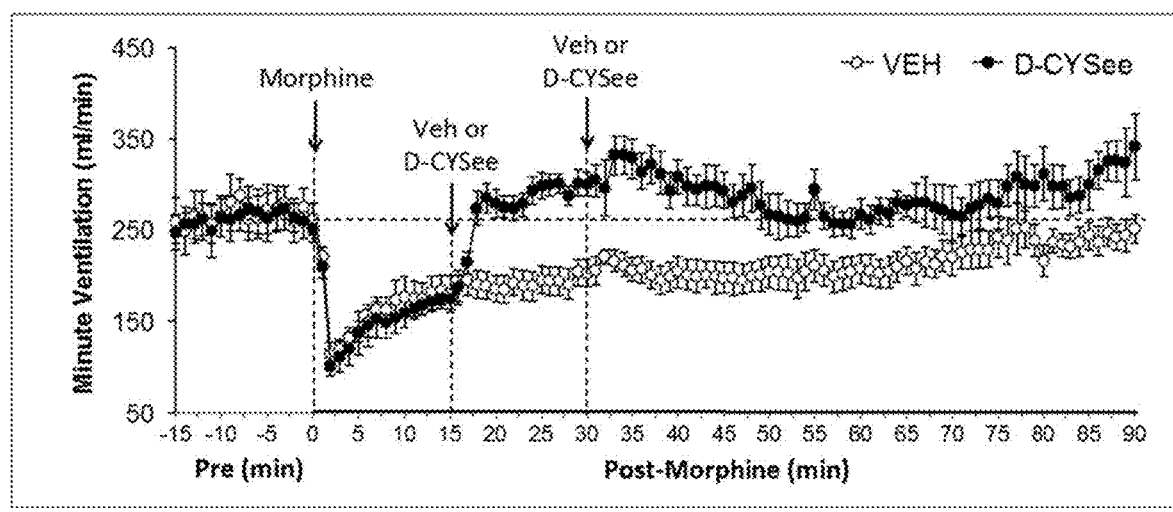
Figure 7B:
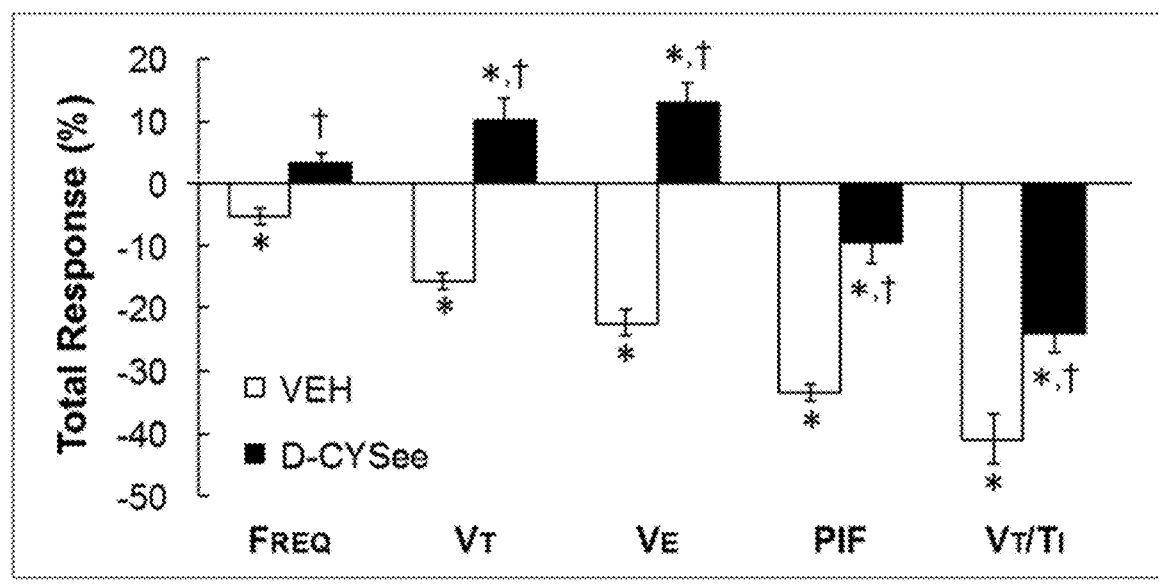

FIGS. 7(A-B) illustrate a plot and graph showing ventilatory responses including tidal volume/inspiratory time (Vt/Ti) elicited by vehicle (saline) or D-CYSee (2×500 µmol/kg, i.v.) in rats which had received a bolus dose of morphine (10 mg/kg, i.v.). There were 9 rats in each group. Data are mean±SEM. *P<0.05, difference from pre-values. †P<0.05, D-Cystine diME versus vehicle.

Figure 8A:
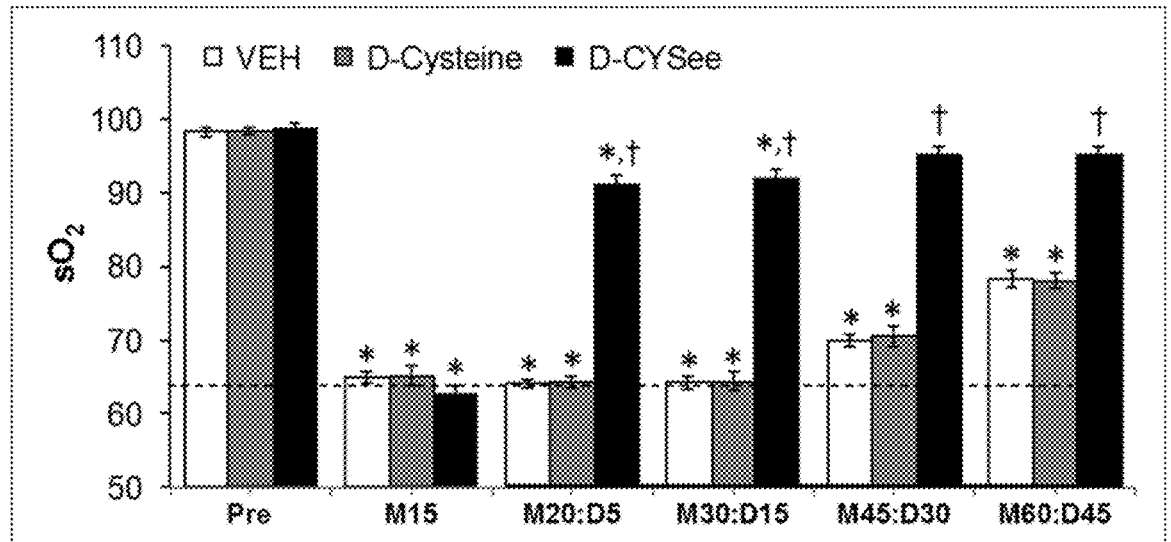
Figure 8B:
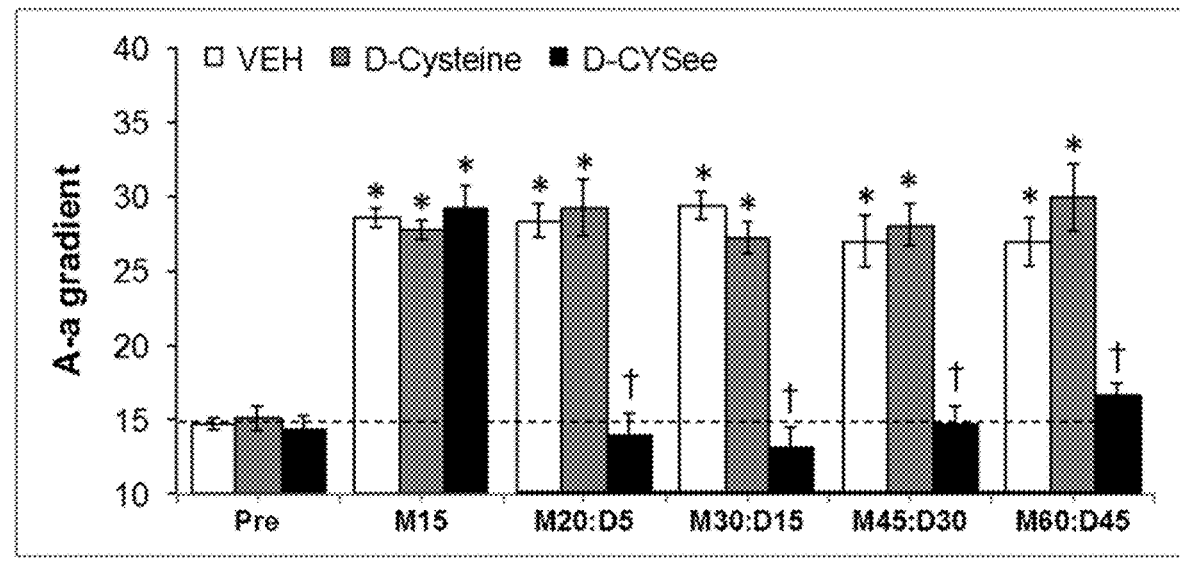
Figure 9A:
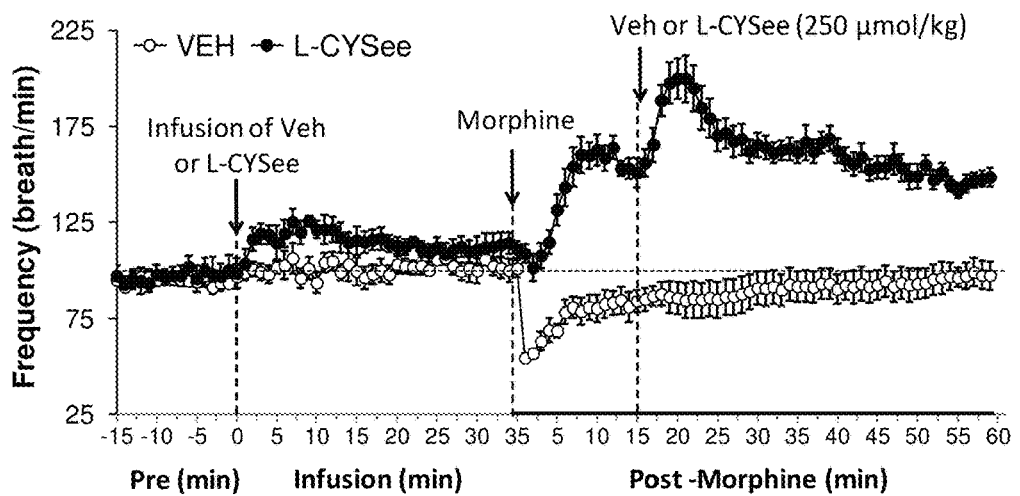
Figure 9B:
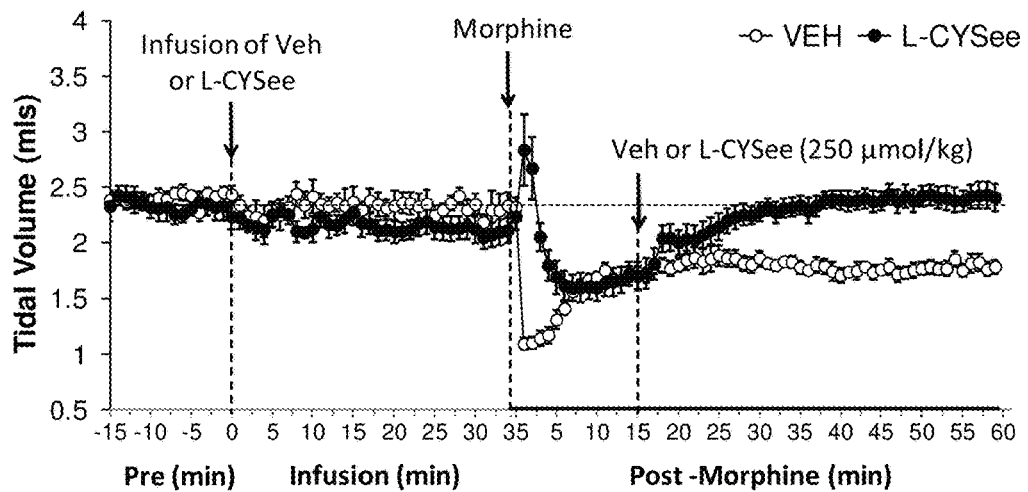
Figure 9C:
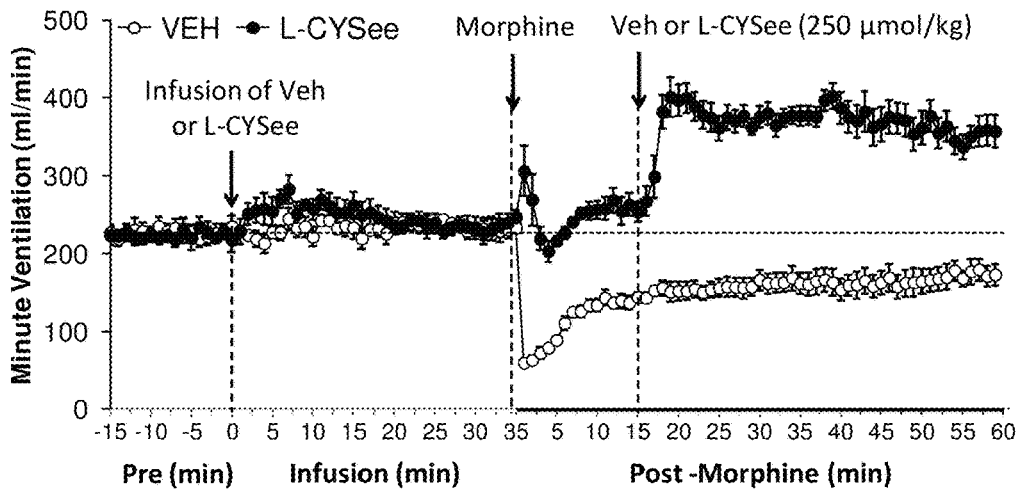
Figure 9D:
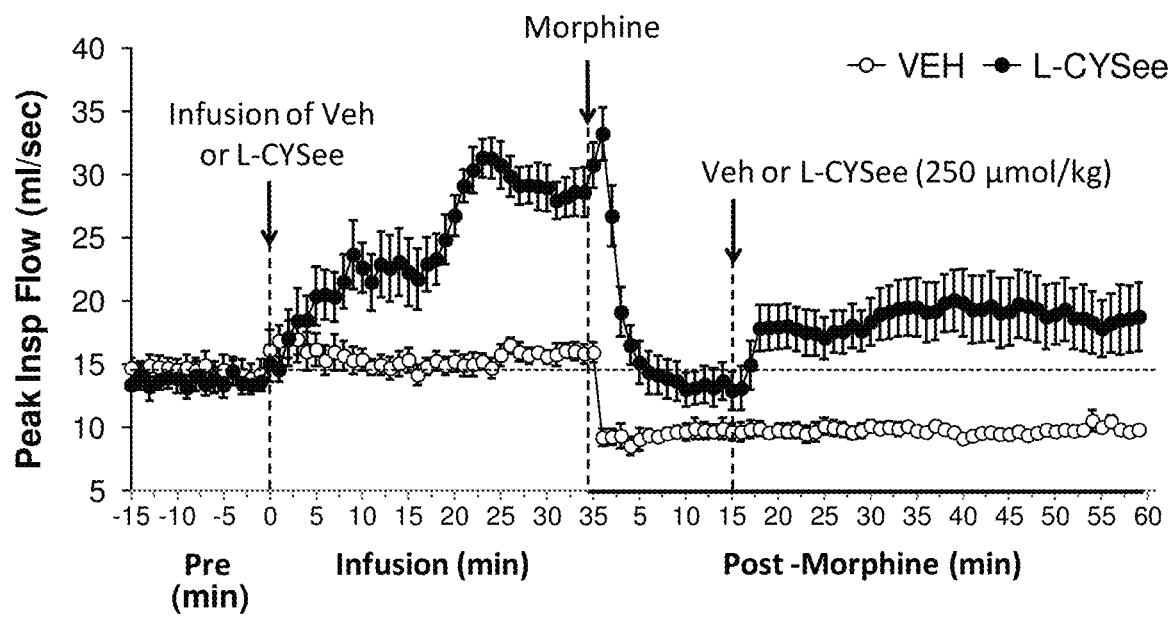
Figure 9E:
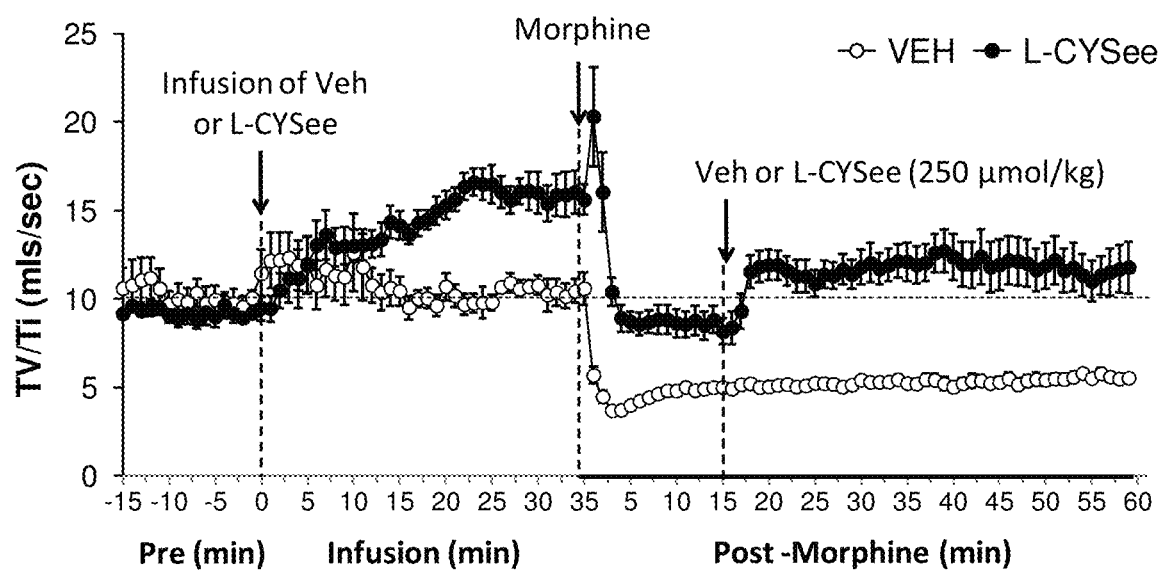

FIGS. 8(A-B) illustrate graphs showing the effects of D-Cysteine (500 µmol/kg, i.v.) and D-CYSee (500 µmol/kg, i.v.) on arterial blood-gas chemistry and A-a gradients in rats which had received an injection of morphine (10 mg/kg, i.v.). Data are presented mean±SEM (n=9 rats per group). *P<0.05, difference from pre-values. †P<0.05, D-Cysteine or D-CYSee versus vehicle.

FIGS. 9(A-E) illustrate plots showing the effects of prior infusion of L-CYSee (total dose of 500 µmol/kg, i.v.) on the ventilatory depressant effects of morphine (10 mg/kg, i.v.) in conscious rats. Responses elicited by a bolus injection of L-CYSee (250 µmol/kg, i.v.) are also shown. Data are presented mean±SEM (n=9 rats per group).

Figure 10A:
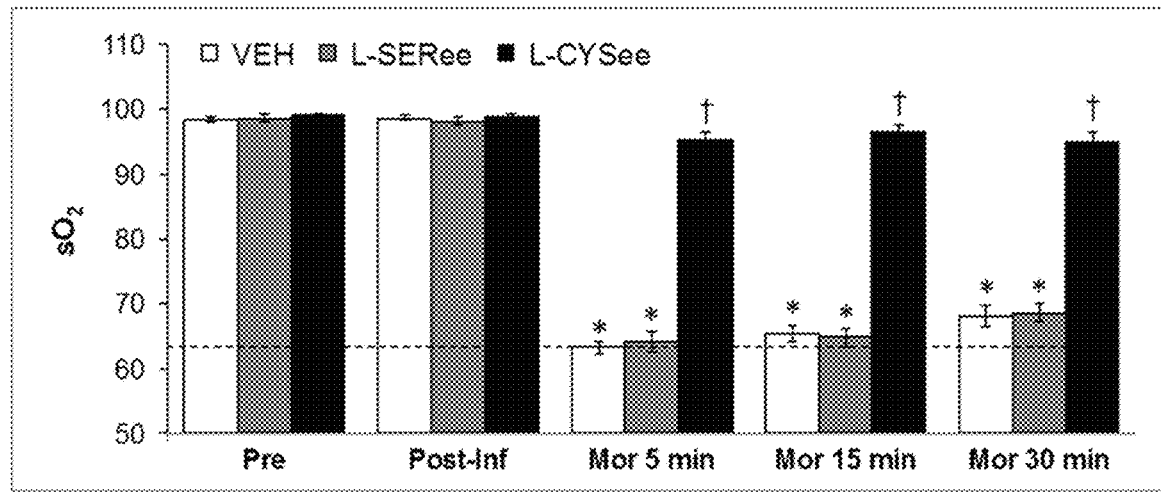
Figure 10B:
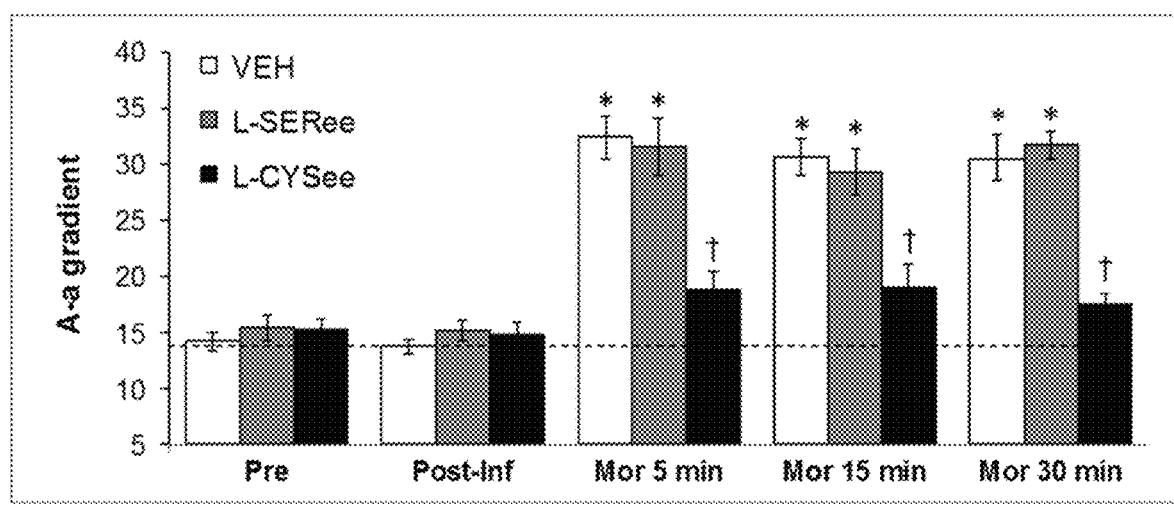

FIGS. 10(A-B) illustrate graphs showing the effects of prior infusion of L-SERee or L-CYSee (total dose of 500 µmol/kg, i.v.) on changes in arterial blood-gas chemistry and A-a gradient elicited by morphine (10 mg/kg, i.v.) in conscious rats. Data are presented mean±SEM (n=9 rats per group). *P<0.05, difference from pre-values. †P<0.05, L-SERee or L-CYSee versus vehicle.

Figure 11A:
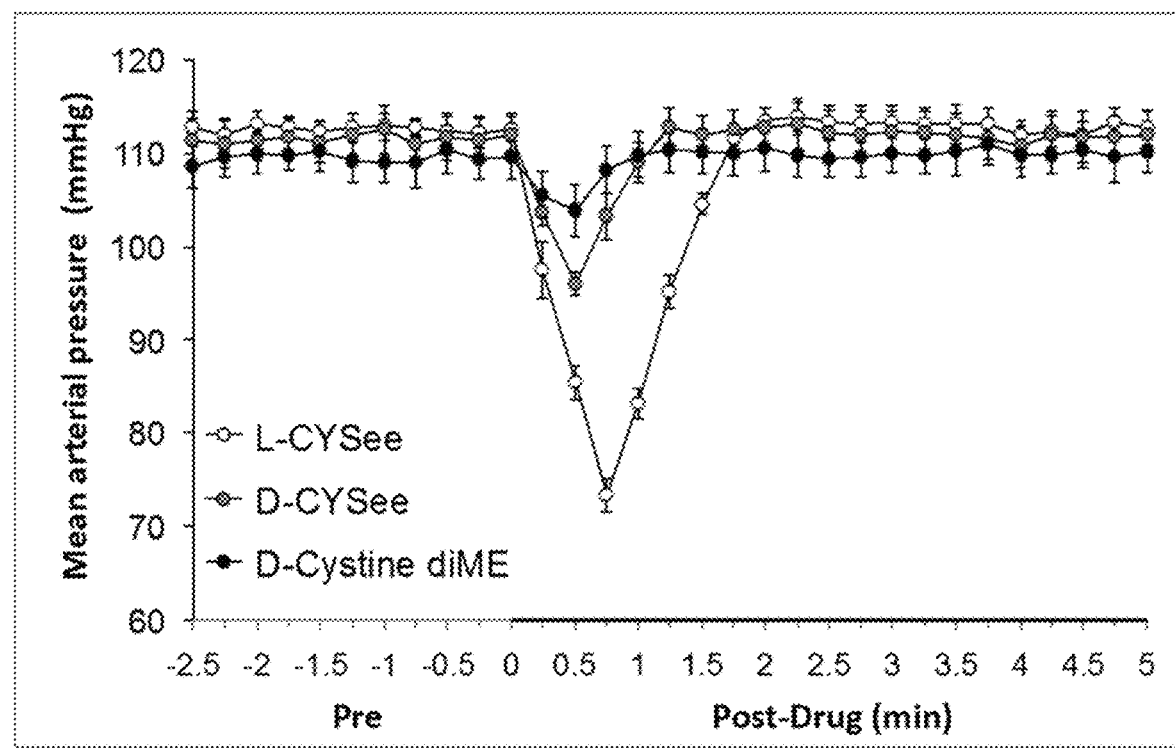
Figure 11B:
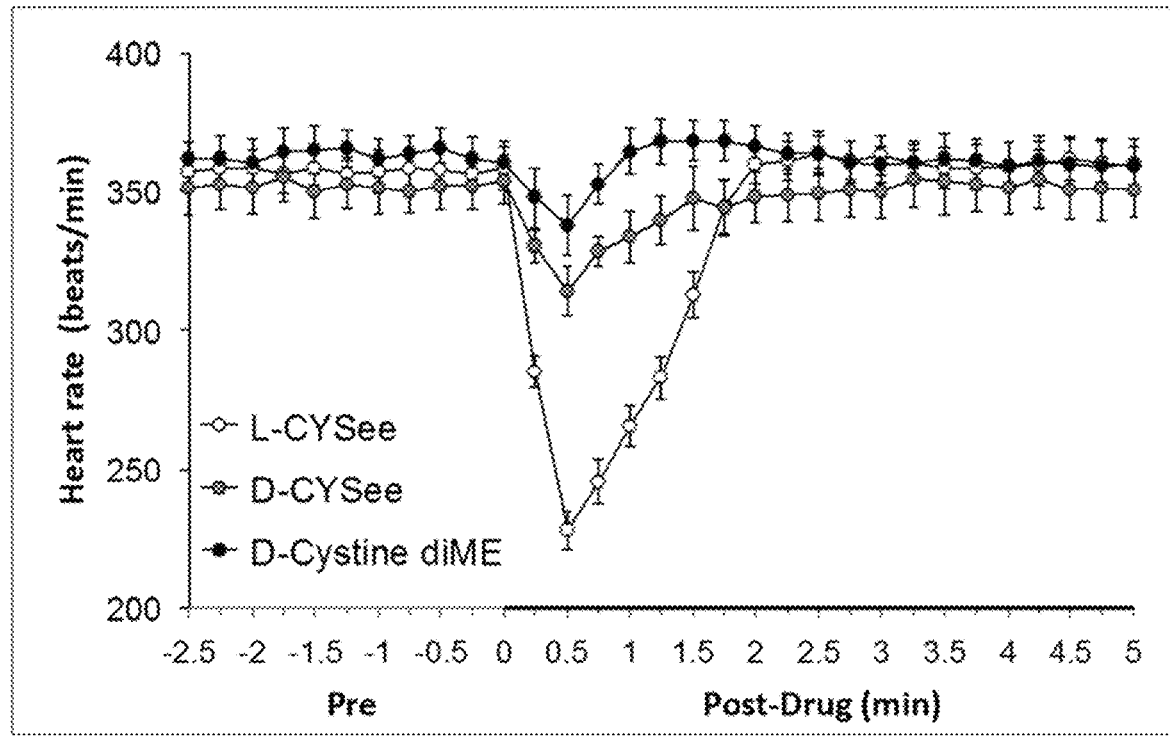
Figure 11C:
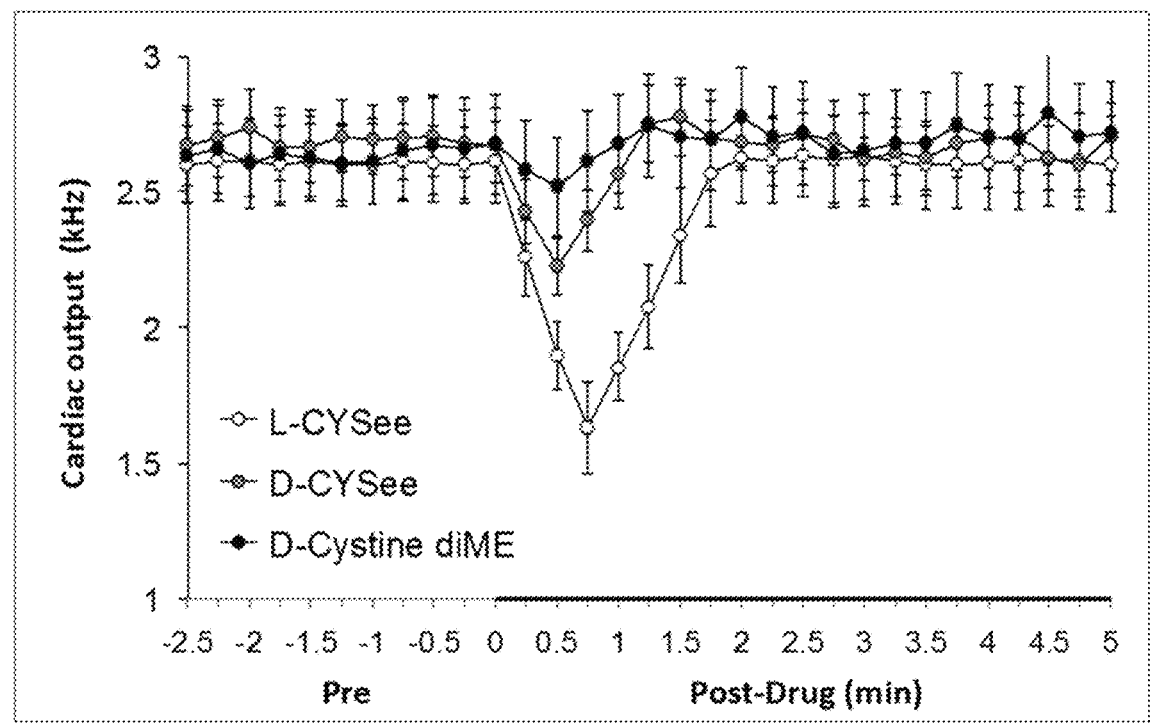

FIGS. 11(A-C) illustrate plots showing the effects of test agents (500 µmol/kg, i.v.) on hemodynamic variables. Data are presented mean±SEM (n=8 rats per group). D-Cystine diME did not elicit significant responses (P>0.05 for all comparisons to Pre).

Figure 12:
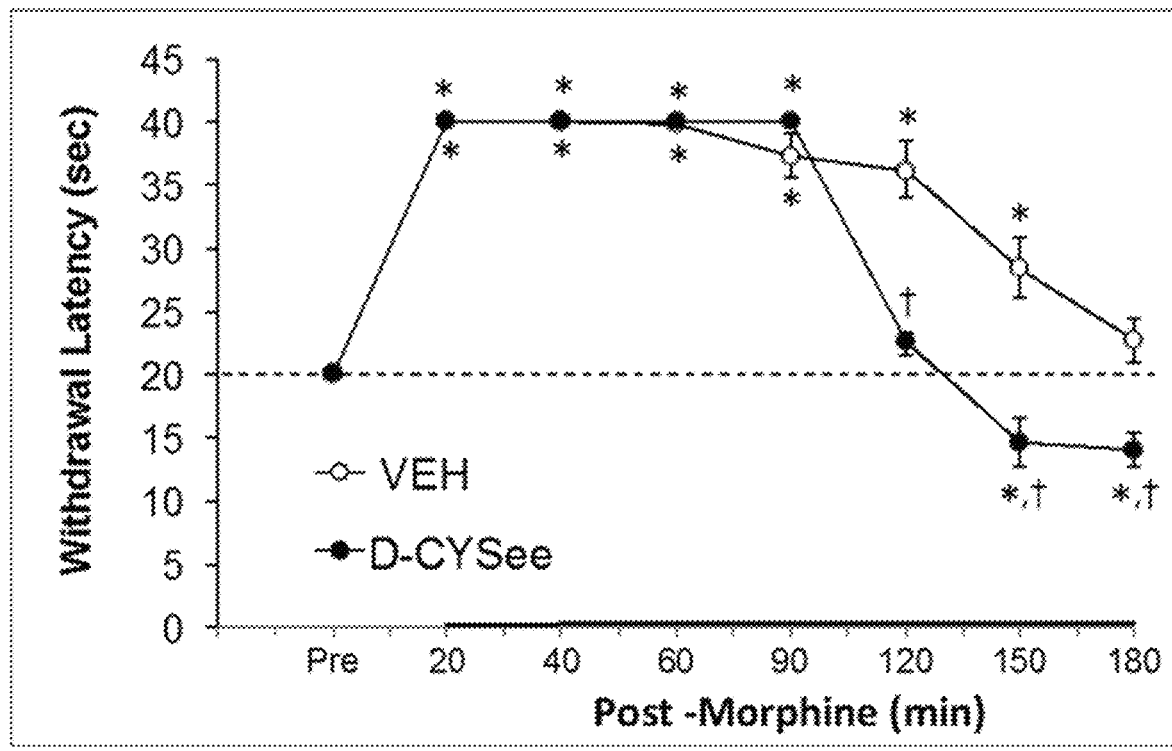

FIG. 12 illustrates a plot showing the effects of pretreatment with D-CYSee (500 µmol/kg, i.v.) on morphine-induced (5 mg/kg, i.v.) analgesia (paw withdrawal latency assay) in conscious rats. The data are presented as mean±SEM (n=6 rats per group). *P<0.05, difference from pre-values. †P<0.05, D-CYSee versus vehicle.

Figure 13:
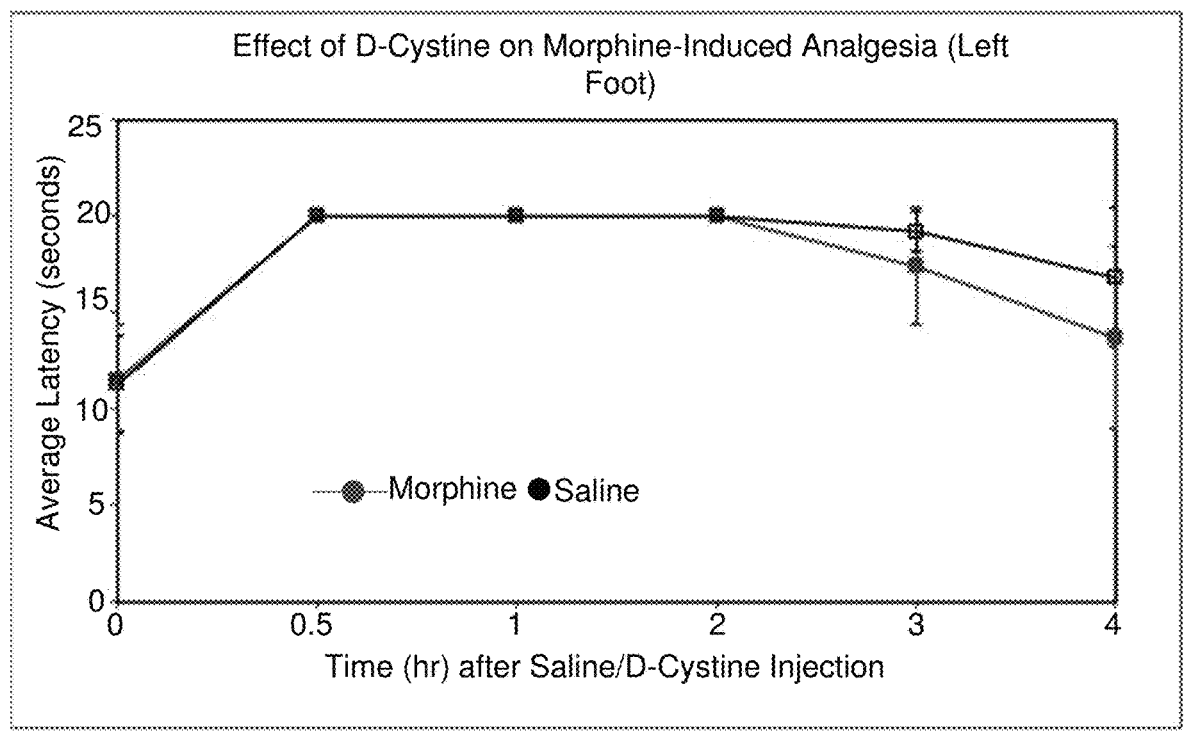

FIG. 13 illustrates a plot showing the effects of D-cystine diME on morphine induced analgesia.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The term "about" or "approximately" as used herein refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" refers to compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substituents, e.g., sulfoxides or sulfinimides, is likewise termed a "chiral center".

The term "chiral isomer" refers to a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2n-1$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric isomers" refers to diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" refers to a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The term "apnea" refers to the absence of normal breathing resulting in intermittent stoppages of breathing.

The term "Cheyne-Stokes respiration" refers to a specific pattern of breathing characterized by a crescendo pattern of breathing that results in apneas and/or hypopneas. A hallmark of this condition is that breathing becomes out of phase with blood oxygen levels.

The term "patency" refers to the state or condition of an airway being open or unblocked.

The term "hypopnea" is similar in many respects to apnea; however, breathing does not fully stop but is partially stopped (i.e., less than 100% of normal breathing, but more than 0% of normal breathing). Hypopnea is also referred to herein as "partial apnea" and can be subdivided into obstructive, central or mixed types.

The term "hypoxia" refers to a deficiency in the amount of oxygen, being taken in by an organism, as well as to a deficiency in the amount of oxygen, which is transported to tissues in an organism.

The term "normoxia" refers to a homoeostasis or "normal condition" regarding the amount of oxygen being taken in by an organism, as well as to a homeostasis or "normal condition" with respect to the amount of oxygen which is transported to tissues in an organism.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In some embodiments, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In some embodiments, the compound or active ingredient is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials, which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt.

One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl)ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

A "patient," "subject," or "host" to be treated by the compounds or methods described herein may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compounds. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament", "active ingredient", and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —CH$_2$CH$_2$—, i.e., a C$_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "C$_1$-C$_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and al kylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —CF$_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S=O), a single bond without charges (S—O) or a single bond with charges [S(+)—O(−)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO—), carbamoyl (—(CO)—NH$_2$), mono-(C$_1$-C$_{24}$ alkyl)-substituted carbamoyl (—(CO)—NH(C$_1$-C$_{24}$ alkyl)), di-(C$_1$-C$_4$ alkyl)-substituted carbamoyl (—(CO)—N(C$_1$-C$_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato isocyanato (—ON$^+$C$^-$), isothiocyanato (—S—CN), azido (—N═N$^+$═N$^-$), formyl (—(CO)—H), thioformyl (—(CS)—H), amino (—NH$_2$), mono- and di-(C$_1$-C$_{24}$ alkyl)-substituted amino, mono- and di-(C$_5$-C$_{20}$ aryl)-substituted amino, C$_2$-C$_{24}$ alkylamido (—NH—(CO)-alkyl), C$_6$-C$_{20}$ arylamido (—NH—(CO)-aryl), imino (—CR═NH where R═hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR═N(alkyl), where R═hydrogen, alkyl, aryl, alkaryl, etc.), arylimino (—CR═N(aryl), where R═hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$ aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties C$_1$-C$_{24}$ alkyl, C$_2$-C$_{24}$ alkenyl, C$_2$-C$_{24}$ alkynyl, C$_5$-C$_{20}$ aryl, C$_6$-C$_{24}$ alkaryl, and C$_6$-C$_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

Embodiments described herein relate to compositions and methods of stimulating ventilatory and/or respiratory drive in a subject in need thereof, and particularly relates to compositions methods of treating breathing diseases and/or disorders associated with impaired ventilator and/or respiratory drive.

In some embodiments, the methods can include stimulating ventilatory and/or respiratory drive in a subject in need thereof by administering to the subject a therapeutically effective amount of a composition comprising a cystine ester, prodrugs thereof, or a pharmaceutically acceptable salt thereof.

It was found that cystine esters, such as cystine alkyl esters (e.g., cystine dialkyl ester, cystine dimethyl ester or cystine diethyl ester) are potent stimulants of ventilatory and/or respiratory drive that effectively overcome breathing disorders, such as narcotic induced respiratory depression. Advantageously, cystine esters described herein can stimulate respiratory drive and overcome respiratory narcotic-induced respiratory depression in a subject in need thereof without impairing, attenuating, and/or adversely affecting narcotic-induced analgesia in the subject.

In some embodiments, the cystine esters described herein can be administered to a subject in need thereof at an amount or therapeutically effective amount to stimulate the ventilatory and/or respiratory drive of the subject, including increasing tidal volume and respiratory frequency, and treat breathing disorders in a subject associated with impaired ventilatory and/or respiratory drive.

In some embodiments, the cystine ester can have the formula:

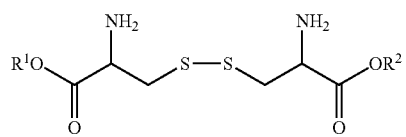

where R$^1$ and R$^2$ are the same or different and are selected from the group consisting of H, unsubstituted or substituted C$_1$-C$_{24}$ alkyl, C$_2$-C$_{24}$ alkenyl, C$_2$-C$_{24}$ alkynyl, C$_3$-C$_{20}$ aryl, heterocycloalkenyl containing from 5-6 ring atoms (wherein from 1-3 of the ring atoms is independently selected from N, NH, N(C$_1$-C$_6$ alkyl), NC(O)(C$_1$-C$_6$ alkyl), O, and S), heteroaryl containing from 5-14 ring atoms, (wherein from 1-6 of the ring atoms is independently selected from N, NH, N(C$_1$-C$_3$ alkyl), O, and S), and heterocyclyl containing from 5-14 ring atoms (wherein from 1-6 of the ring atoms is independently selected from N, NH, N(C$_1$-C$_3$ alkyl), O, and S), and at least one of R$^1$ and R$^2$ is not a H; prodrugs thereof, or pharmaceutically acceptable salts thereof.

In some embodiments, R$^1$ and R$^2$ are independently H or an unsubstituted or substituted C$_1$-C$_{24}$ alkyl, wherein at least one of R$^1$ and R$^2$ is not a H. In other embodiments, R$^1$ and $R^2$ are independently selected from the group consisting of H, methyl, ethyl, propyl, and butyl, and at least one of $R^1$ and $R^2$ is not a H.

In other embodiments, the cystine ester can be a cystine dialkyl ester, prodrug thereof, or pharmaceutically acceptable salt thereof. The cystine dialkyl ester can comprise a mixture at least one of D or L isomers of a cystine dialkyl ester. For example, the cystine dialkyl ester can comprise a mixture of: less than about 50% by weight of the D isomer of a cystine dialkyl ester and greater than about 50% by weight of the L isomer of a cystine dialkyl ester, less than about 25% by weight of the D isomer of a cystine dialkyl ester and greater than about 75% by weight of the L isomer of a cystine dialkyl ester, less than about 10% by weight of the D isomer of a cystine dialkyl ester and greater than about 90% by weight of the L isomer of a cystine dialkyl ester, less than about 1% by weight of the D isomer of a cystine dialkyl ester and greater than about 99% by weight of the L isomer of a cystine dialkyl ester, greater than about 50% by weight of the D isomer of a cystine dialkyl ester and less than about 50% by weight of the L isomer of a cystine dialkyl ester, greater than about 75% by weight of the D isomer of a cystine dialkyl ester and less than about 25% by weight of the L isomer of a cystine dialkyl ester, greater than about 90% by weight of the D isomer of a cystine dialkyl ester and less than about 10% by weight of the L isomer of a cystine dialkyl ester, or greater than about 99% by weight of the D isomer of a cystine dialkyl ester and less than about 1% by weight of the L isomer of a cystine dialkyl ester.

In a still further embodiment, the cystine dialkyl ester can consist essentially of or consist of the D isomer of cystine dialkyl ester. In yet another embodiment, the cystine dialkyl ester can consist essentially of or consist of the L isomer of cystine dialkyl ester.

In some embodiments, the cystine dialkyl ester is a D-cystine dialkyl ester, prodrug thereof, or pharmaceutically acceptable salt thereof. Advantageously, it was found that D-isomer can be more active than the corresponding L-isomer of the cystine dialkyl ester and unlike L-cysteine do not increase upper airway resistance or promote cystinosis-like effects in animals or have negative cardiovascular effects of L-cysteine esters. The D-cystine dialkyl ester can be selected from the group consisting of D-cystine dimethyl ester, D-cystine diethyl ester, combinations thereof, prodrugs thereof, and pharmaceutically acceptable salts thereof.

Composition comprising the cystine esters described herein can be administered to a subject to stimulate ventilatory and/or respiratory drive in a subject in need thereof. In some embodiments, the subject can have or is at increased risk of impaired ventilatory and/or respiratory drive associated with a disorder or breathing disorder, such as respiratory depression, including narcotic, sedative, and/or anesthetic, induced respiratory drive or suppresses ventilatory drive, sleep apnea (central, mixed and obstructive including but not limited to co-existing conditions of heart failure, kidney disease and stroke), sleep-disordered breathing (especially with snoring and arousals), apnea of prematurity, allergies, neurological or neuromuscular diseases (e.g., stroke or amyotrophic lateral sclerosis (ALS)), weakened respiratory muscles, hypoventilation due to stroke, trauma, surgery and/or radiation, obesity-hypoventilation syndrome, primary alveolar hypoventilation syndrome, acquired central hypoventilation syndromes (ACHS), congenital central hypoventilation syndromes (CCHS), chronic bronchitis, Cheyne-Stokes respiration, dyspnea, altitude sickness or acclimatization to high altitude, hypopnea, hypoxia, hypercapnia, cystic fibrosis, chronic obstructive pulmonary disease (COPD), nasal septum deformation, tonsillitis, adenoiditis, and Arnold-Chiari syndrome. The composition can be administered to the subject at an amount effective to treat and/or prevent the breathing disorder or impaired ventilatory and/or respiratory drive associated with the disorder or breathing disorder.

In some embodiments, the composition can be administered to the subject to prevent the need for mechanical ventilation in subjects with acutely impaired ventilatory and/or respiratory drive because of an acute exacerbation of an underlying lung disease or an acute requirement for narcotic analgesia. For example, the subjects can be at-risk subjects with severe, hypercapneic COPD or mixed apnea evident on polysomnography.

In other embodiments, the subject can have or has an increased risk of respiratory depression or suppressed ventilatory drive that is caused, for example, by an anesthetic, a sedative, anxiolytic agent, a hypnotic agent, alcohol, and/or a narcotic. By way of a non-limiting example, narcotic analgesics (e.g., morphine, fentanyl, oxycodone, buprenorphine) are administered to cancer patients to alleviate pain. The dose is often limited by a fear of respiratory depression. In addition, even a partial respiratory depression from these drugs causes hypoxia and a resulting excessive daytime sleepiness that can be debilitating and severely decrease quality of life. General anesthetics can exert a similar depressant effect on respiration and delay a patient's transfer from the operating room to a surgical recovery area. A composition comprising a cystine ester described herein is therefore useful to counteract the lingering effects of the anesthetic, and for restoring adequate respiratory drive to enable the patient to breathe on their own.

In other embodiments, a composition including the cystine ester can be administered in ambulatory delivery formulations to treat respiratory depression associated with narcotics, analgesics, sedatives, and/or opioids. The subject can be one who is taking and/or over-dosed on the narcotics, analgesics, sedatives, and/or opioids and who is experiencing or at risk of acute respiratory depression. The compositions can be administered to the subject to treat stimulate ventilatory and/or respiratory drive and increase breathing frequency.

In some embodiments, compositions comprising the cystine esters described herein can be administered to subject in combination with at least one additional compound, agent, and/or therapeutic agent useful for treating the subject or the breathing disorder. These additional compounds, agents, and/or therapeutic agents can include commercially available agents or compounds, known to treat, prevent, or reduce the symptoms of breathing disorders or treat the disorder in the subject.

In some embodiments, the at least one additional therapeutic agent can change normal breathing in a subject. Such additional agents can be selected from the group consisting of doxapram and enantiomers thereof, acetazolamide, almitrine, theophylline, caffeine, methylprogesterone and related compounds, sedatives that decrease arousal threshold in sleep disordered breathing patients, sodium oxybate, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, and combinations thereof.

In other embodiments, compositions comprising the cystine esters described herein and at least one additional compound has additive, complementary or synergistic effects in the treatment of the breathing disorder or other disorder in the subject. In a non-limiting example, the compositions comprising the cystine esters described herein may be used concurrently or in combination with one or more of the following drugs: doxapram, enantiomers of doxapram, acetazolamide, almitrine, theophylline, caffeine, methylprogesterone and related compounds, sedatives that decrease arousal threshold in sleep disordered breathing patients (such as eszopiclone and zolpidem), sodium oxybate, benzodiazepine receptor agonists (e.g., zolpidem, zaleplon, eszopiclone, estazolam, flurazepam, quazepam, temazepam, triazolam), orexin antagonists (e.g., suvorexant), tricyclic antidepressants (e.g., doxepin), serotonergic modulators, adenosine and adenosine receptor and nucleoside transporter modulators, cannabinoids (such as, but not limited to, dronabinol), orexins, melatonin agonists (such as ramelteon) and compounds known as ampakines.

Non-limiting examples of ampakines are the pyrrolidine derivative racetam drugs such as piracetam and aniracetam; the "CX—" series of drugs which encompass a range of benzoylpiperidine and benzoylpyrrolidine structures, such as CX-516 (6-(piperidin-1-yl-carbonyl)quinoxaline), CX-546 (2,3-dihydro-1,4-benzodioxin-7-yl-(1-piperidyl)-methanone), CX-614 (2H,3H,6aH-pyrrolidino(2,1-3',2')-1, 3-oxazino-(6',5'-5,4)benzo(e)1,4-diox-an-10-one), CX-691 (2,1,3-benzoxadiazol-6-yl-piperidin-1-yl-methanone), CX-717, CX-701, CX-1739, CX-1763, and CX-1837; benzothiazide derivatives, such as cyclothiazide and IDRA-21 (7-chloro-3-methyl-3,4-dihydro-2H-1,2,4-benzothiadiazine 1,1-dioxide); biarylpropylsulfonamides, such as LY-392, 098, LY-404,187 (N-[2-(4'-cyanobiphenyl-4-yl)propyl]propane-2-sulfonamide), LY-451,646 and LY-503,430 (4'-{(1S)-1-fluoro-2-[(isopropylsulfonyl)amino]-1-methylethyl}-N-methylbi-phenyl-4-carboxamide).

The combination of two or more compounds may refer to a composition wherein the individual compounds are physically mixed or wherein the individual compounds are physically separated. A combination therapy encompasses administering the components separately to produce the desired additive, complementary or synergistic effects.

In one embodiment, the composition comprising the cystine esters described herein and the agent are physically mixed in the composition. In another embodiment, the composition comprising the cystine esters described herein and the agent are physically separated in the composition.

In one embodiment, compositions comprising the cystine esters described herein are co-administered with a compound that is used to treat another disorders but causes loss of breathing control. In this aspect, compositions comprising the cystine esters described hereinblock or otherwise reduce depressive effects on normal breathing control caused by the compound with which they are co-administered. Such compound that treats another disorder but depresses breathing control includes but is not limited to anesthetics, sedatives, sleeping aids, anxiolytics, hypnotics, alcohol, and narcotic analgesics. The co-administered compound may be administered individually, or a combined composition as a mixture of solids and/or liquids in a solid, gel or liquid formulation or as a solution, according to methods known to those familiar with the art.

In one embodiment, a composition comprising the cystine esters described herein is co-administered with at least one additional compound useful for treating breathing control disorders and with at least one compound that is used to treat other disorder but causes a loss of breathing control. In this aspect, the compound of the invention works in an additive, complementary or synergistic manner with the co-administered breathing control agent to block or otherwise reduce depressive effects on normal breathing control caused by other compounds with which they are combined. A synergistic effect may be calculated, for example, using suitable methods.

In some embodiments, a composition comprising the cystine esters described herein may be packaged with at least one additional compound useful for treating breathing control disorders. In another embodiment, a composition comprising the cystine esters described herein may be packaged with a therapeutic agent known to cause changes in breathing control, such as, but not limited to, anesthetics, sedatives, anxiolytics, hypnotics, alcohol, and narcotic analgesics. A co-package may be based upon, but not limited to, dosage units.

The cystine esters and/or additional compounds or agents described herein can be provided in a pharmaceutical composition with a pharmaceutically acceptable carrier or excipient. In some embodiment, pharmaceutical compositions that include the cystine esters described herein may be formulated to deliver a dose to the subject of between 1 ng/kg/day and 100 mg/kg/day. In another embodiment, the pharmaceutical compositions may be administered to deliver a dose of between 1 ng/kg/day and 500 mg/kg/day.

The relative amounts of the cystine esters or active ingredient, the pharmaceutically acceptable carrier, and any additional ingredients in a pharmaceutical composition can vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods described herein may be suitably developed for nasal, inhalational, oral, rectal, vaginal, pleural, peritoneal, parenteral, topical, transdermal, pulmonary, intranasal, buccal, ophthalmic, epidural, intrathecal, intravenous or another route of administration. Other contemplated formulations include projected nanoparticles, microspheres, liposomal preparations, coated particles, and polymer conjugates.

In one embodiment, the compositions comprising the cystine esters described herein are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions, which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions is contemplated include, but are not limited to, humans and other primates, mammals including commercially relevant mammals such as cattle, pigs, horses, sheep, cats, and dogs.

In one embodiment, the compositions described herein are formulated using one or more pharmaceutically acceptable excipients or carriers Pharmaceutically acceptable carriers, which are useful, include, but are not limited to, glycerol, water, saline, ethanol, recombinant human albumin, solubilized gelatins, and other pharmaceutically acceptable salt solutions, such as phosphates and salts of organic acids. Examples of these and other pharmaceutically acceptable carriers are described in Remington's Pharmaceutical Sciences (1991, Mack Publication Co., New Jersey).

In some embodiments, the carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Formulations of the compositions described herein may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition may comprise a preservative from about 0.005% to 2.0% by total weight of the composition. The preservative is used to prevent spoilage in the case of exposure to contaminants in the environment. Examples of preservatives include but are not limited to those selected from the group consisting of benzyl alcohol, sorbic acid, parabens, imidurea and combinations thereof. A particularly preservative is a combination of about 0.5% to 2.0% benzyl alcohol and 0.05% to 0.5% sorbic acid.

The composition can include an antioxidant and a chelating agent which inhibit the degradation of the compound. Examples of antioxidants for some compounds are BHT, BHA, alpha-tocopherol and ascorbic acid in the range of about 0.01% to 0.3% by weight by total weight of the composition. The chelating agent can be present in an amount of from 0.01% to 0.5% by weight by total weight of the composition. Examples of chelating agents include edetate salts (e.g., disodium edetate) and citric acid in the weight range of about 0.01% to 0.20% by weight by total weight of the composition. The chelating agent is useful for chelating metal ions in the composition, which may be detrimental to the shelf life of the formulation.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. An "oily" liquid is one which comprises a carbon-containing liquid molecule and which exhibits a less polar character than water. Liquid solutions of the pharmaceutical composition may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition may also be prepared, packaged, or sold in the form of oil-in-water emulsion or a water-in-oil emulsion. The oily phase may be a vegetable oil, such as olive or *arachis* oil, a mineral oil, such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

The regimen of administration may affect what constitutes an effective amount. The therapeutic formulations may be administered to the patient either prior to or after the onset of a breathing disorder event. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions described herein to a patient, preferably a mammal, more preferably a human, may be carried out using known procedures, at dosages and for periods of time effective to modulate breathing control and/or respiratory and ventilatory drive in the patient. An effective amount of the therapeutic compound sufficient to achieve a therapeutic effect may vary according to factors, such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound s from about 0.01 mg/kg to 100 mg/kg of body weight/per day. One of ordinary skill in the art would be able to study the relevant factors and make the determination regarding the effective amount of the therapeutic compound without undue experimentation.

The compositions comprising the cystine esters described herein may be administered to an animal as frequently as several times daily, or it may be administered less frequently, such as once a day, once a week, once every two weeks, once a month, or even less frequently, such as once every several months or even once a year or less. It is understood that the amount of composition or cystine esters described herein dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms are dictated by and directly dependent on (a) the unique characteristics of the therapeutic compound and the particular therapeutic effect to be achieved, and (b) the limitations inherent in the art of compounding/formulating such a therapeutic compound for the treatment of breathing disorders in a patient.

In one embodiment, the compositions are administered to the patient in dosages that range from one to five times per day or more. In another embodiment, the compositions are administered to the patient in range of dosages that include, but are not limited to, once every day, every two days, every three days to once a week, and once every two weeks. It will be readily apparent to one skilled in the art that the frequency of administration of the various combination compositions will vary from subject to subject depending on many factors including, but not limited to, age, disease or disorder to be treated, gender, overall health, and other factors.

Compounds for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound is from about 0.5 µg and about 5,000 mg. In some embodiments, a dose of a compound used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

Other embodiments described herein relate to a packaged pharmaceutical composition comprising a container holding a therapeutically effective amount of a compound, alone or in combination with a second pharmaceutical agent; and instructions for using the compound to treat, prevent, or reduce one or more symptoms of breathing disorder in a patient.

The term "container" includes any receptacle for holding the pharmaceutical composition or for managing stability or water uptake. For example, in one embodiment, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a breathing disorder in a patient.

Routes of administration of any of the compositions include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions are not limited to the particular formulations and compositions that are described herein.

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS) pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation. Hard capsules comprising the active ingredient may be made using a physiologically degradable composition, such as gelatin. The capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin from animal-derived collagen or from a hypromellose, a modified form of cellulose, and manufactured using optional mixtures of gelatin, water and plasticizers such as sorbitol or glycerol. Such soft capsules comprise the active ingredient, which may be mixed with water or an oil medium such as peanut oil, liquid paraffin, or olive oil.

For oral administration, the compositions comprising the cystine esters described herein may be in the form of tablets or capsules prepared by conventional means with pharmaceutically acceptable excipients, such as binding agents;

fillers; lubricants; disintegrates; or wetting agents. If desired, the tablets may be coated using suitable methods and coating materials.

A tablet comprising the active ingredient may, for example, be made by compressing or molding the active ingredient, optionally with one or more additional ingredients. Compressed tablets may be prepared by compressing, in a suitable device, the active ingredient in a free-flowing form, such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semisolid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

In some embodiments, the composition can be provided in the form of a multilayer tablet comprising a layer providing for the delayed release of one or more compounds useful within the methods described herein, and a further layer providing for the immediate release of one or more compounds useful within the methods. Using a wax/pH-sensitive polymer mix, a gastric insoluble composition may be obtained in which the active ingredient is entrapped, ensuring its delayed release.

Liquid preparations for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition, which are suitable for oral administration may be prepared, packaged, and sold either in liquid form or in the form of a dry product intended for reconstitution with water or another suitable vehicle prior to use.

Parenteral administration of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition that can be used for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices, such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form in a recombinant human albumin, a fluidized gelatin, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Formulations for topical administration include, but are not limited to, liquid or semi-liquid preparations, such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (i.e., U.S. Pat. No. 6,323,219).

In alternative embodiments, the topically active pharmaceutical composition may be optionally combined with other ingredients, such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

A pharmaceutical composition may be prepared, packaged, or sold in a formulation for buccal administration. Such formulations may be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, can have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those skilled in the art.

In one embodiment, the composition is designed to promote controlled release of the drug, such that the location, extent and rate of exposure of the compound when administered are modulated. Factors that affect the target zone for exposure of an orally administered drug may be the drug's pH and enzymatic stability, reactivity with other drugs (e.g., certain antibiotics), solubility as a salt or free base, ionization behavior, and pharmacodynamic and pharmacokinetic behaviors in specific environments.

Controlled- or sustained-release formulations of a pharmaceutical composition may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions.

Controlled-release of an active ingredient can be stimulated by various inducers, for example water, pH, temperature, enzymes, bacteria, or other physiological conditions or compounds.

In certain embodiments, the formulations of described herein may be, but are not limited to, short-term, rapid-offset, as well as controlled, for example, sustained release, delayed release and pulsatile release formulations. The active drug substance can also be coated on an implantable medical device to be eluted or be released using a remotely activated system.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation (drug embedded in polymeric matrices).

In some embodiments, the compounds described herein are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 24 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 24 hours, about 12 hours, about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 24 hours, about 12 hours, about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

In some embodiments, compounds described herein are formulated with an enteric coating, which has been modified by adding plasticizers to the polymer before coating. The plasticizers may be added to adjust resistance to chipping or cracking of the coating, while also lowering the glass transition temperature of the coating to enable smoothness and even spreadability of the coating during its application. Suitable plasticizers include polyethylene glycol 8000 (PEG 8000), triethyl citrate (TEC), and triacetin, which may be incorporated into the polymeric enteric coating agent.

Compounds described herein may be enterically formulated under a variety of dosage forms, including (but not limited to) capsules, granules of the active drug itself, beads, micro spheres, and tablets. In one embodiment, the composition comprises a drug encapsulated in a capsule enterically coated to release the drug in the duodenum or other intestinal environment. In another embodiment, pharmaceutically acceptable capsules include hard capsules. In yet another embodiment, pharmaceutically acceptable capsules include soft gelatin capsules.

In some embodiments, a composition comprising the cystine esters described herein is encapsulated in pure granular or powdered form, with no carriers, excipients or other pharmaceutically acceptable additives. In another embodiment, a compound described herein is encapsulated together with one or more pharmaceutically acceptable carriers, excipients, antioxidants, antifungals, (e.g., benzoic and ascorbic acids and their salts, and phenolic compounds such as methyl, ethyl, propyl and butyl p-hydroxybenzoate (parabens)), antimicrobial preservatives, colorants, and flavorants. The excipients may aid in capsule-filling behavior, stability, and in the distribution of the drug when the capsule disintegrates in the body. In another embodiment, granules and/or powders of a compound are enterically coated before being placed in a capsule. The enterically coated granules and/or powders placed in the capsule may feature one or several types of enteric coating to enable delivery of the drug to different regions of the intestine. The capsule may lack enteric coating or may be coated with an enteric coating that is the same as or distinct from the coating applied to any of the enterically coated materials inside the capsule.

In one embodiment, a composition comprising the cystine esters described herein is encapsulated in a liquid in the form of a solution or suspension in water or various pharmaceutically acceptable oils or other dispersion medium, optionally with such excipients as cosolvents (e.g., PEG 300, PEG 400, propylene glycol, glycerol, tween 80, ethanol), solubility enhancers (e.g., sorbitol, dextrose), wetting agents (e.g., thickening agents), buffers (e.g., disodium hydrogen phosphate), antioxidants, antifungals, preservatives, colorants and flavorants. In one embodiment, a composition comprising the cystine esters described herein is formulated for liquid filled capsules in the form of the pure drug as granules and/or powders in the liquid. In another embodiment, the capsule containing the composition in liquid is enterically coated. In yet another embodiment, granules and/or powders of a compound are enterically coated before being placed in a liquid and the combination placed in a capsule. The enterically coated granules and/or powder may feature one or several types of enteric coating to enable delivery of the drug to distinct regions of the intestine. The capsule may lack enteric coating or may be coated with an enteric coating that is the same as or distinct from the coating applied to any of the enterically coated materials inside the capsule.

In one embodiment, a composition comprising the cystine esters described hereinis encapsulated in a capsule comprised of material that affords post-gastric drug delivery without the need for the separate application of an enteric coating (e.g., Entericare enteric softgels). The composition may be encapsulated in such capsules as granules or powders with or without excipients, and as solutions or suspensions as described above.

In one embodiment, the solid particles of a compound, as a variety of particle sizes and particle size distributions, are admixed with excipients, such as microcrystalline cellulose or lactose and formed as a bead that comprises the drug-containing core onto which the enteric coating is applied. In another embodiment, a compound is formed as a suspension or solution including, optionally, buffers (e.g., aq. 1 N HCl with tris(hydroxymethyl)aminomethane "TRIS"), and binders (e.g., Opadry Clear Coat Powder) and coated onto a base particle, for example sugar beads (e.g., Sugar Spheres, NF particles) to form a bead. In yet another embodiment, the beads are enterically coated. In yet another embodiment, a compound is formulated as enterically coated beads, as described above, and the beads further formulated by encapsulation. In yet another embodiment, a combination of beads with different types of enteric coating is encapsulated, such that once released from the capsule, the compound is made available in a controlled manner at different regions ranging from the duodenum to other parts of the intestine. The capsule may lack enteric coating or may be coated with an enteric coating that is the same as or distinct from the coating applied to any of the enterically coated materials inside the capsule.

In one embodiment, a composition comprising the cystine esters described herein is formulated as tablets or caplets which alone or in combination with other formulation components deliver drug to the duodenum or other intestinal region. In another embodiment, a composition comprising the cystine esters described herein is formulated as tablets or caplets that are enterically coated and that constitute the dosage form administered. In yet another embodiment, tablets or caplets of suitable size and shape are placed inside a capsule. In yet another embodiment, the capsule is enterically coated and contains non-enterically coated tablets or caplets, which are released from the capsule in the duodenum or other intestinal region. In yet another embodiment, the capsule is designed to disintegrate in the stomach and release entericallly coated tablets or caplets for subsequent delivery to duodenum or other intestinal regions. In yet another embodiment, the capsule and tablets or caplets contained within are both enterically coated to provide further control over the release of the tablets or caplets from the capsule, and the subsequent release of the drug from the tablet or caplet. In yet another embodiment, tablets or caplets featuring a variety of enteric coating are combined and placed in a capsule which itself may optionally be enterically coated as well. Materials useful for enteric coatings for tablets and caplets include but are not limited to those described above for application to capsules.

Enteric coatings may permit premature drug release in acidic media. In one embodiment, a compound of the present invention is formulated such that a subcoating is applied before the enteric coating is applied. The subcoating may comprise application to the enteric substrate of a soluble subcoating agent, examples of which are hydroxypropylmethylcellulose, povidone, hydroxypropyl cellulose, polyethylene glycol 3350, 4500, 8000, methyl cellulose, pseudo ethylcellulose and amylopectin. It is understood that similar type of synthetic and semisynthetic polymeric products from other companies may be used. A thin subcoating layer on the enteric substrate impedes water penetration through the enteric coating on the capsule shell or into the core where the active ingredient is located, preventing premature drug release. The subcoating may also promote the release of the drug in a basic environment by moderating the acidic microenvironment at the interface between the core and the enteric coating. In one embodiment, a compound is formulated with a subcoating containing organic acids intended to promote more rapid polymer dissolution of a capsule as the coating degrades in environments with pH 5-6, promoting a rapid release of the drug in basic media.

Other embodiments described herein relate to a method of treating a subject in need thereof, such as a subject without normal ventilation and/or normal breathing control, by administering the compositions comprising the cystine esters described herein, and additionally treating the patient using a device to support breathing. Such devices include, but are not limited to, ventilation devices, CPAP and BiPAP devices.

Mechanical ventilation is a method to mechanically assist or replace spontaneous breathing. Mechanical ventilation is typically used after an invasive intubation, a procedure wherein an endotracheal or tracheostomy tube is inserted into the airway. It is normally used in acute settings, such as in the ICU, for a short period of time during a serious illness. It may also be used at home or in a nursing or rehabilitation institution, if patients have chronic illnesses that require long-term ventilation assistance. The main form of mechanical ventilation is positive pressure ventilation, which works by increasing the pressure in the patient's airway and thus forcing air into the lungs. Less common today are negative pressure ventilators (for example, the "iron lung") that create a negative pressure environment around the patient's chest, thus sucking air into the lungs. Types of mechanical ventilation are: conventional positive pressure ventilation, high frequency ventilation, non-invasive ventilation (non-invasive positive pressure ventilation or NIPPY), proportional assist ventilation (PAY), adaptive servo ventilation (ASV) and neurally adjusted ventilatory assist (NAVA).

Non-invasive ventilation refers to all modalities that assist ventilation without the use of an endotracheal tube. Non-invasive ventilation is primarily aimed at minimizing patient discomfort and the complications associated with invasive ventilation, and is often used in cardiac disease, exacerbations of chronic pulmonary disease, sleep apnea, and neuromuscular diseases. Non-invasive ventilation refers only to the patient interface and not the mode of ventilation used; modes may include spontaneous or control modes and may be either pressure or volume cycled modes.

Some commonly used modes of NIPPY include continuous positive airway pressure (CPAP). This kind of machine has been used mainly by patients for the treatment of sleep apnea at home, but now is in widespread use across intensive care units as a form of ventilatory support. The CPAP machine stops upper airway obstruction by delivering a stream of compressed air via a hose to a nasal pillow, nose mask or full-face mask, splinting the airway open (keeping it open under air pressure) so that unobstructed breathing becomes possible, reducing and/or preventing apneas and hypopneas. When the machine is turned on, but prior to the mask being placed on the head, a flow of air comes through the mask. After the mask is placed on the head, it is sealed to the face and the air stops flowing. At this point, it is only the air pressure that accomplishes the desired result. This has the additional benefit of reducing or eliminating the extremely loud snoring that sometimes accompanies sleep apnea.

Bi-level positive airway pressure (BIPAP) alternate between inspiratory positive airway pressure (IPAP) and a lower expiratory positive airway pressure (EPAP), triggered by patient effort. On many such devices, backup rates may be set, which deliver IPAP pressures even if patients fail to initiate a breath.

The invention is further illustrated by the following example, which is not intended to limit the scope of the claims.

Example

We evaluated a novel class of thiol-based respiratory stimulants. The original compounds made use of the findings that erythrocytic hemoglobin transports not only $CO_2$ and $O_2$, but also thiol-bound nitric oxide (NO), and that erythrocytic thiol-bound NO content decays logarithmically as a function of changes in oxyhemoglobin saturation. Thiol-containing compounds, such as glutathione or N-acetylcysteine (NAC) accelerate loss of NO from deoxyhemoglobin and can serve as potent respiratory stimulants, increasing minute ventilation in humans and animals. N-acetylcysteine signals erythrocytic hemoglobin desaturation and augments hypoxia-induced increases minute ventilation. Relative to placebo, humans receiving oral NAC three times daily had a three-fold greater increase in minute ventilation (24±4% versus 8±3%) when exposed acutely to isocapnic hypoxia. However, high NAC doses were required. We studied the details of this pathway worked out in both rat and transgenic mouse models.

To target this pathway, we screened thiol-containing compounds as respiratory stimulants. We discovered several that were more potent than NAC. Of these, the compounds with the most sustained activity were D-Cystine dimethylester (D-Cystine diME) and D-Cystine diethylester (D-Cystine diEE). We found that oxidized thiols such as D-Cystine diME and D-Cystine diEE may be longer-acting than the corresponding reduced thiols—such as D-Cysteine ethyl ester (D-CYSee)—because they are more stable, with gradual reduction to the active, but shorter-acting, reduced form in vivo; this reduction has previously been demonstrated. The D-isomer may be more active than the corresponding L-isomer because of slower metabolism to intracellular cellular cysteine-containing peptides and proteins—permitting sustained activity. This was the starting premise, but our more recent work suggests additionally that D-Cystine diME may inhibit a specific potassium channel involved in respiratory control. We also found that modifications of the cysteine molecule, including simple N-acetylation, decrease activity. These compounds can be used as a novel treatment option for COPD and other pulmonary patients with acute respiratory depression. The principal target population can include patients with impaired ventilatory and/or respiratory drive who are at risk for requiring mechanical ventilation because of either an acute exacerbation of underlying lung disease or an acute requirement for narcotic analgesia.

Figure 1A:
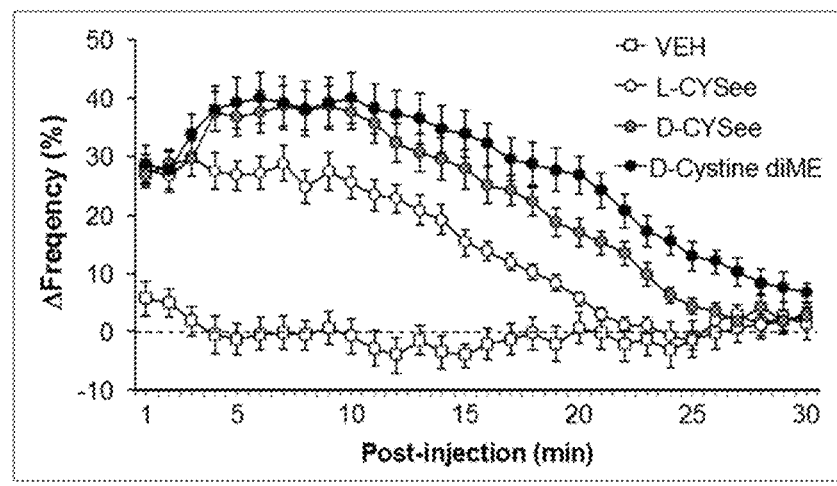
FIGS. 1(A-C) illustrate plots showing the ventilatory responses elicited by vehicle (saline) and test compounds (500 μmol/kg, i.v.) in conscious rats. Each drug was given to a separate group of rats (n=8 per group). Data are presented as mean±SEM.
Figure 1B:
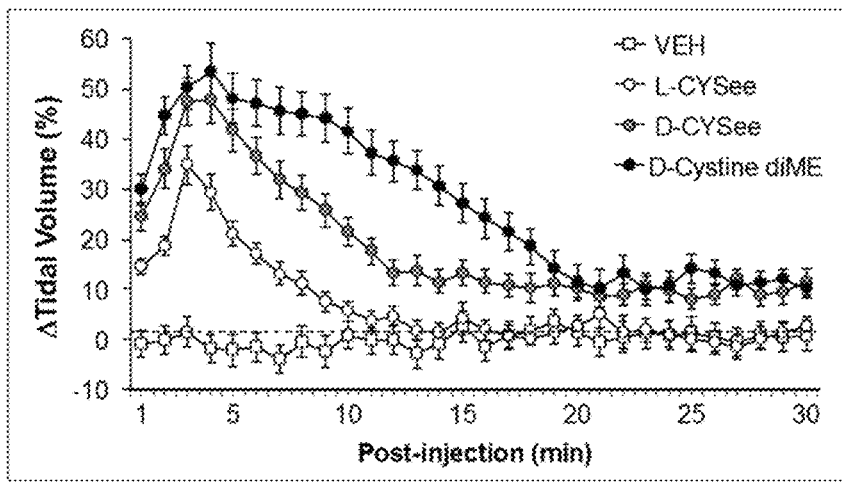
Figure 1C:
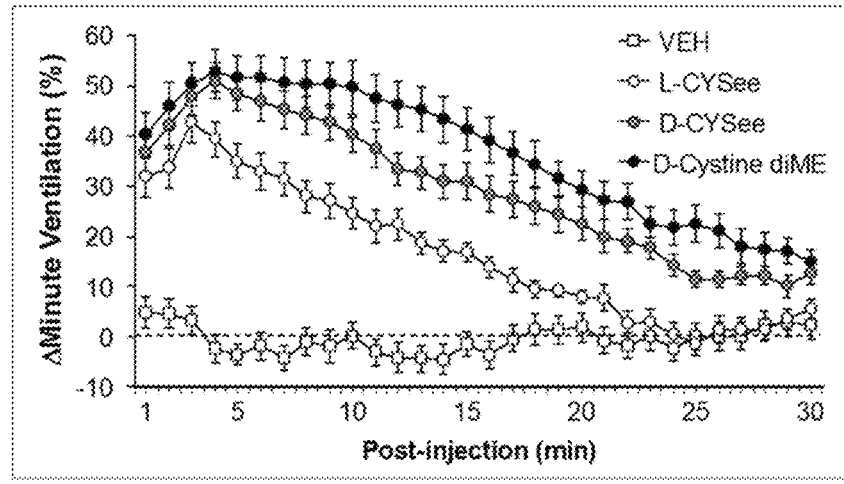

D-Cystine diME Given Parenterally Causes a Sustained Increase in Tidal Volume and Respiratory Frequency in Conscious Rats D-Cystine diME Increases Minute Ventilation in Conscious Rats Plethysmographic measurements in conscious male adult Sprague-Dawley rats revealed that D-Cystine diME (500 µmol/kg, i.v.) elicited robust increases in frequency of breathing, tidal volume and minute ventilation of 20 min in duration (FIG. 1). Identical injections of D-CYSee (D-Cysteine ethyl ester) and L-CYSee (L-Cysteine ethyl ester) had similar effects, but D-Cystine diME provided the most sustained effect. We hypothesize that oxidized D-cystine esters have sustained activity because they are taken up into neuroregulatory cells and erythrocytes, slowly reduced to D-cysteine, but are not inactivated by incorporation into peptides and proteins by enzymes that recognize L-cysteine.

Figure 2A:
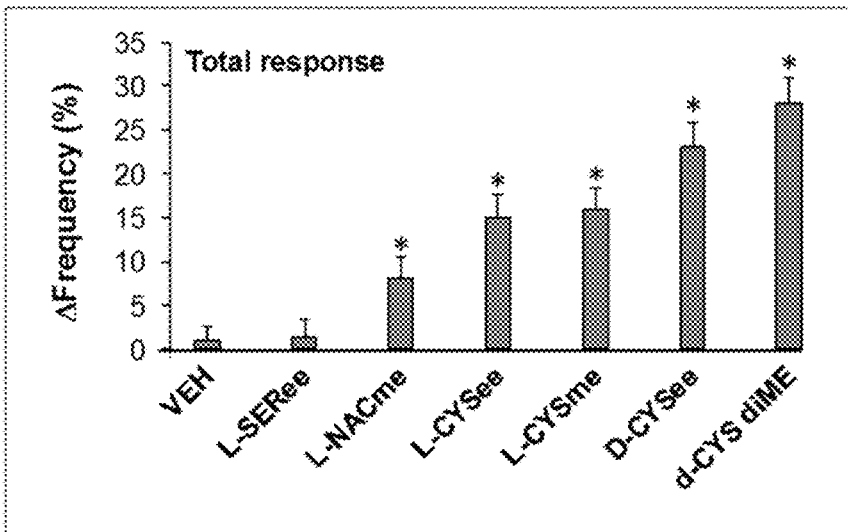
FIGS. 2(A-C) illustrate plots showing the total responses elicited by the test compounds (500 μmol/kg, i.v.) in conscious rats. Each compound was given to a separate group of rats (n=8 rats per group). Data are mean±SEM. *P<0.05, significant response. †P<0.05, d-Cystine diME versus other agents.
Figure 2B:
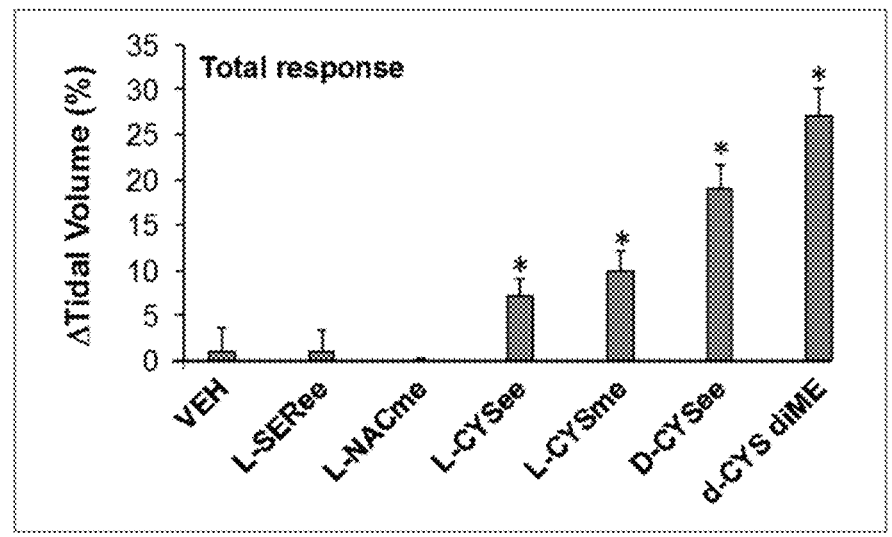
Figure 2C:
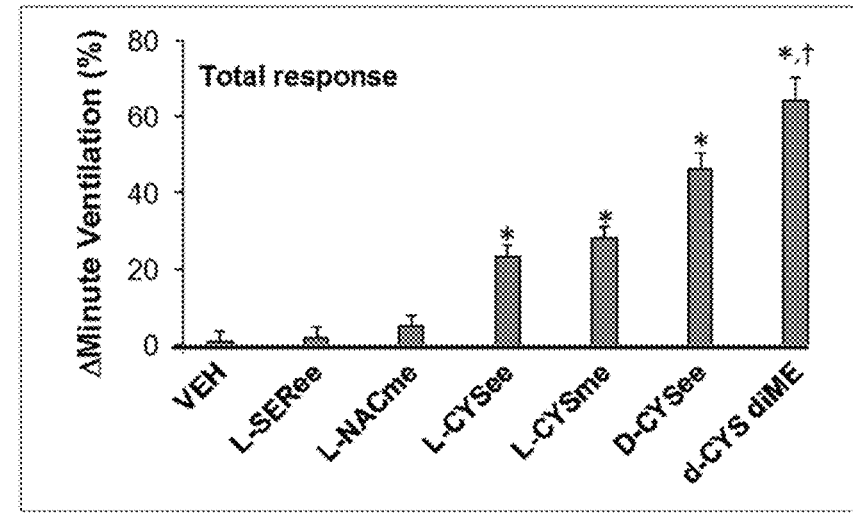

D-Cystine diME is the Most Active Member of this Novel Class of Respiratory Stimulants The total responses recorded over the 30 min post-injection period (% baseline) are summarized in FIG. 2. These data provide structure-activity relationship information. Injection of the vehicle (saline) elicited minor effects. L-serine ethyl ester (L-SERee), was minimally active, demonstrating the key importance of the sulfur atom in these responses. The comparatively minor effects of L-N-acetyl-cysteine methylester (L-NACme) demonstrate that placing acetyl moiety on the nitrogen atom of L-cysteine also impairs efficacy. Of key importance were the findings that (1) L-cysteine methylester (L-CYSme) was as efficacious as L-CYSee (L-Cysteine ethyl ester), (2) D-CYSee (D-Cysteine ethyle ester) was more efficacious that L-CYSee/L-CYSme, and (3) D-Cystine diME was the most efficacious of the test compounds.

Dose-Response Effects of D-Cystine diME in Conscious Rats

Figure 3A:
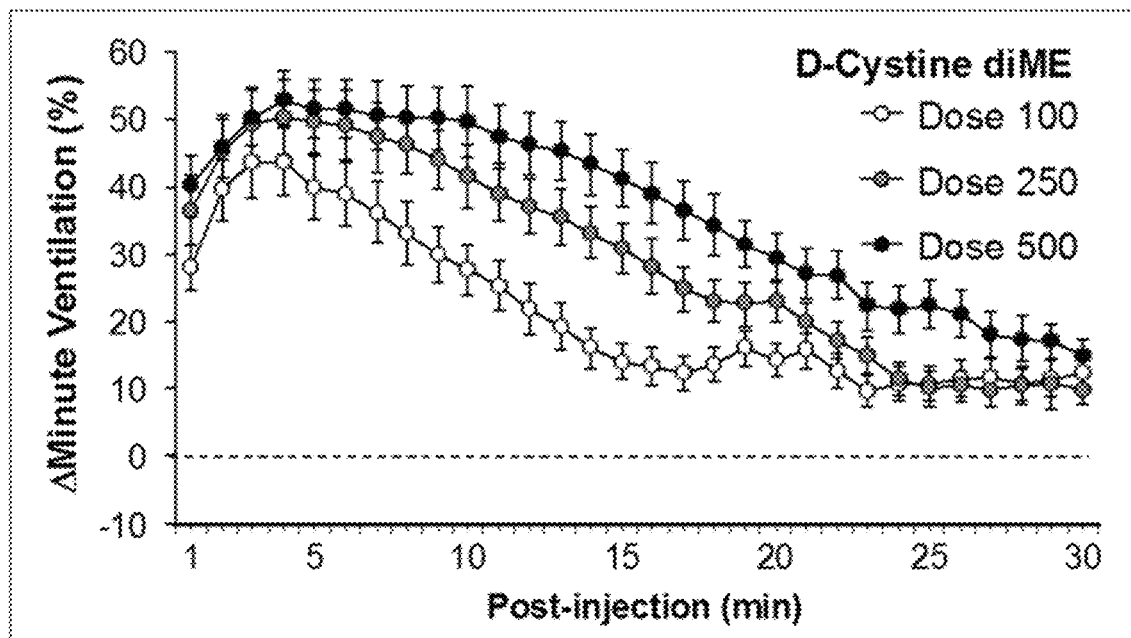
FIGS. 3(A-B) illustrate plots showing dose-dependent changes in ventilatory parameters elicited by D-Cystine diME in conscious rats. Each dose was given to a separate group of rats (n=8 rats per group). The data are presented as mean±SEM.
Figure 3B:
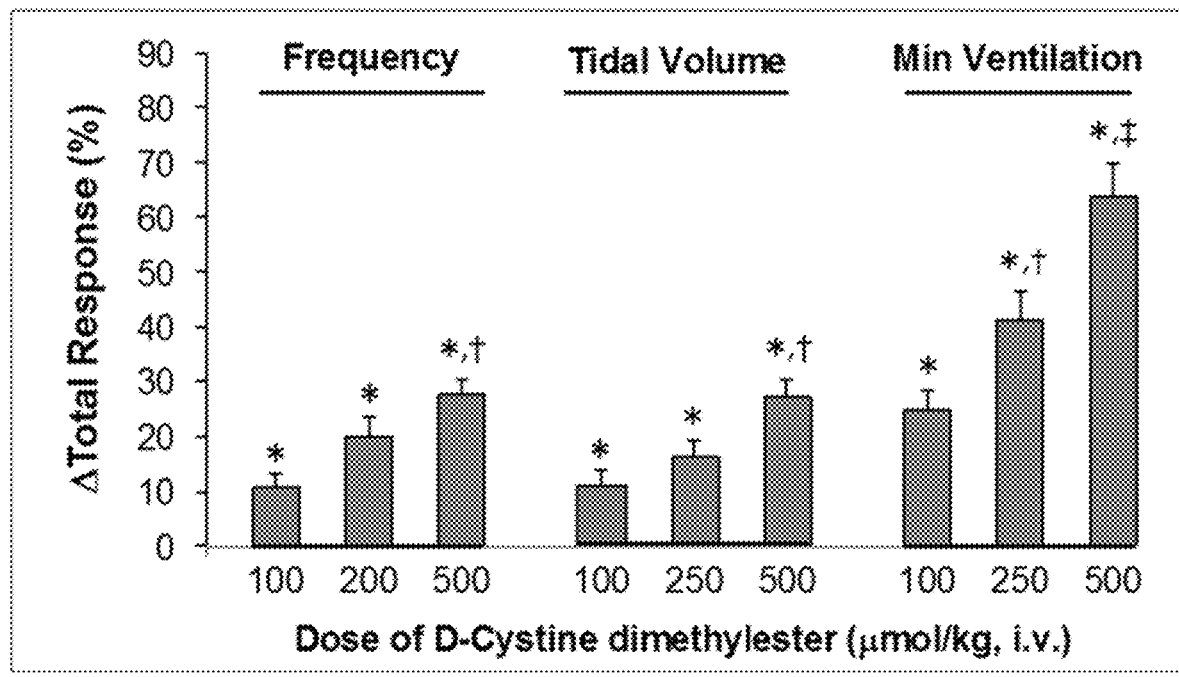

A key feature of therapeutic drug is dose-dependency. As shown in FIG. 3, the ventilatory responses elicited by D-CYS diME clearly dose-dependent.

D-Cystine diME Also Elicits Pronounced Ventilatory Responses in Conscious Mice

Figure 4A:
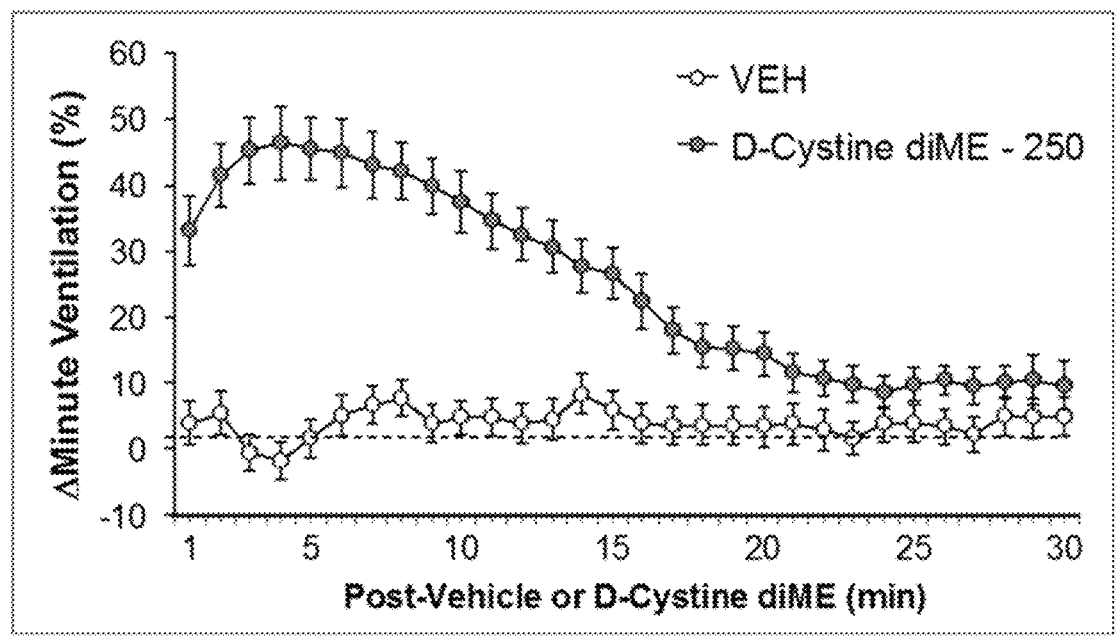
FIGS. 4(A-B) illustrate plots showing ventilatory responses elicited by vehicle (saline) or D-Cystine diME (250 mol/kg, i.v.) in conscious mice. Each drug was given to a separate group of mice (n=8 mice per group). The data are presented as mean±SEM. *P<0.05, significant response. †P<0.05, d-CYS diME versus other agents.
Figure 4B:
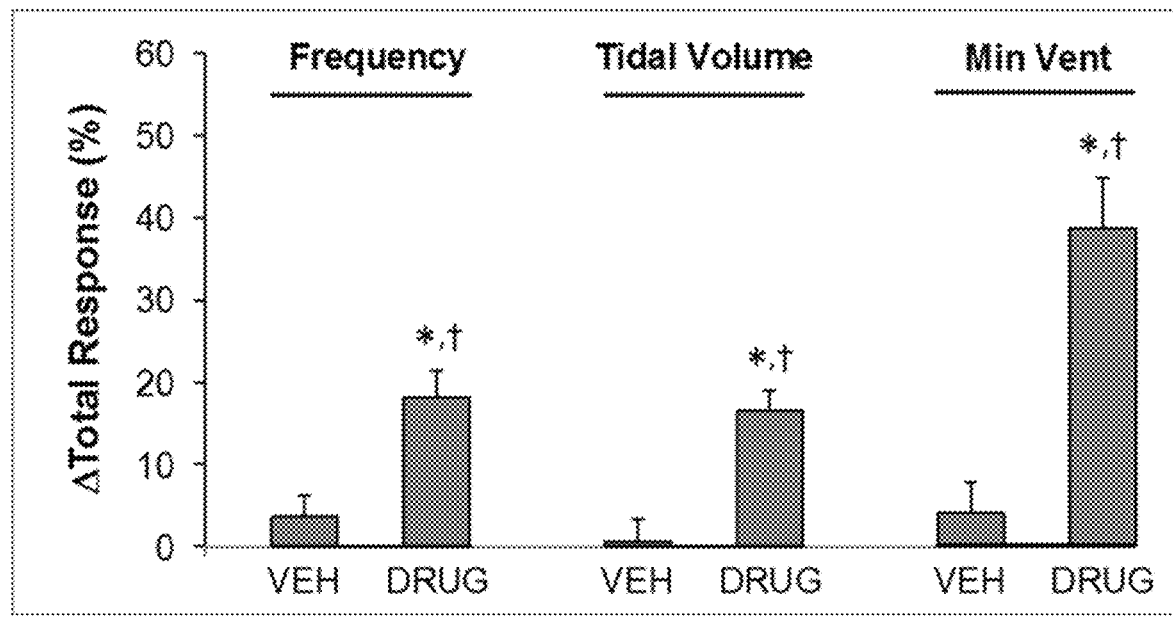
Figure 5A:
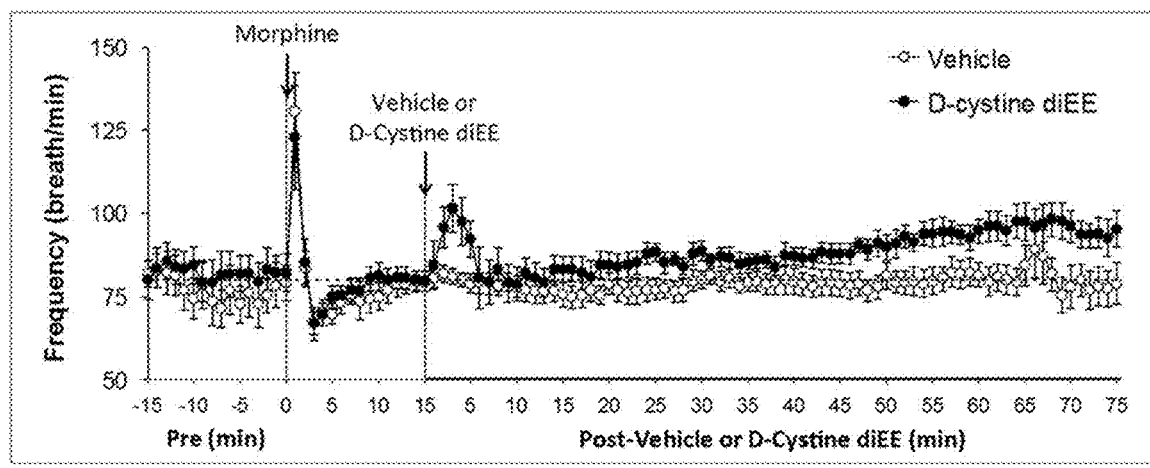
FIGS. 5(A-F) illustrate plots showing ventilatory responses including tidal volume/inspiratory time (Vt/Ti) elicited by vehicle (saline) or D-Cystine diEE (500 μmol/kg, i.v.) in rats which had received a bolus dose of morphine (10 mg/kg, i.v.). There were 9 rats in each group. Data are mean±SEM. *P<0.05, difference from pre-values. †P<0.05, D-Cystine or D-Cystine diME versus vehicle.
Figure 5B:
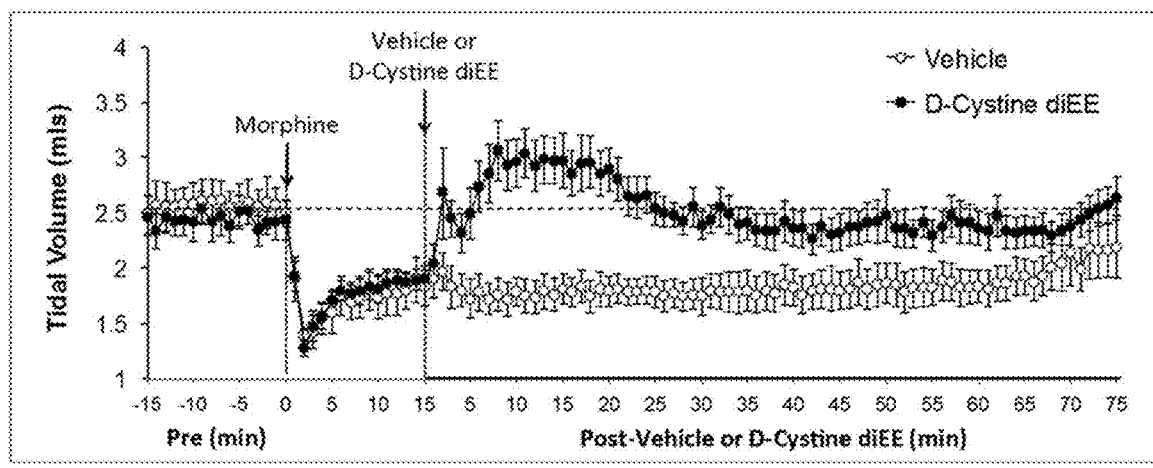
Figure 5C:
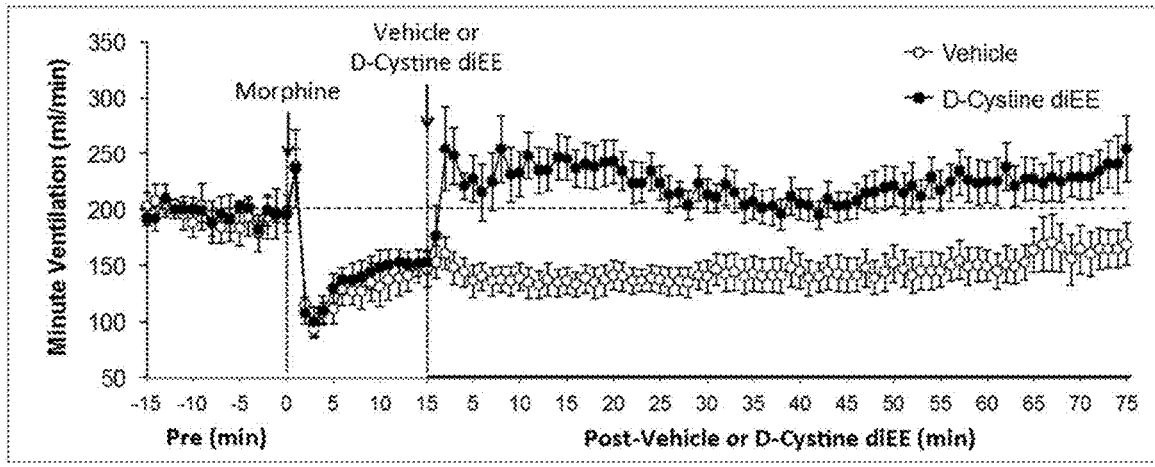
Figure 5D:
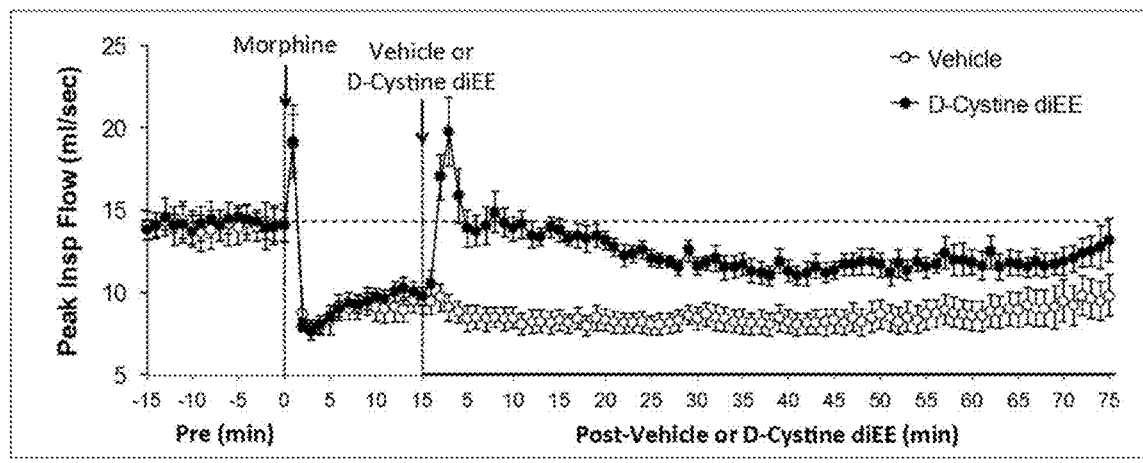
Figure 5E:
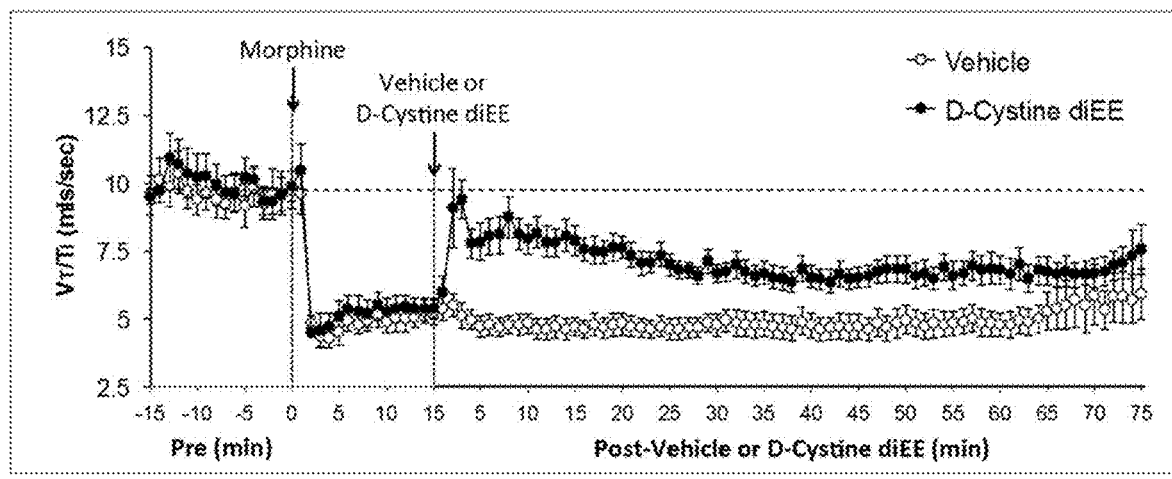
Figure 5F:
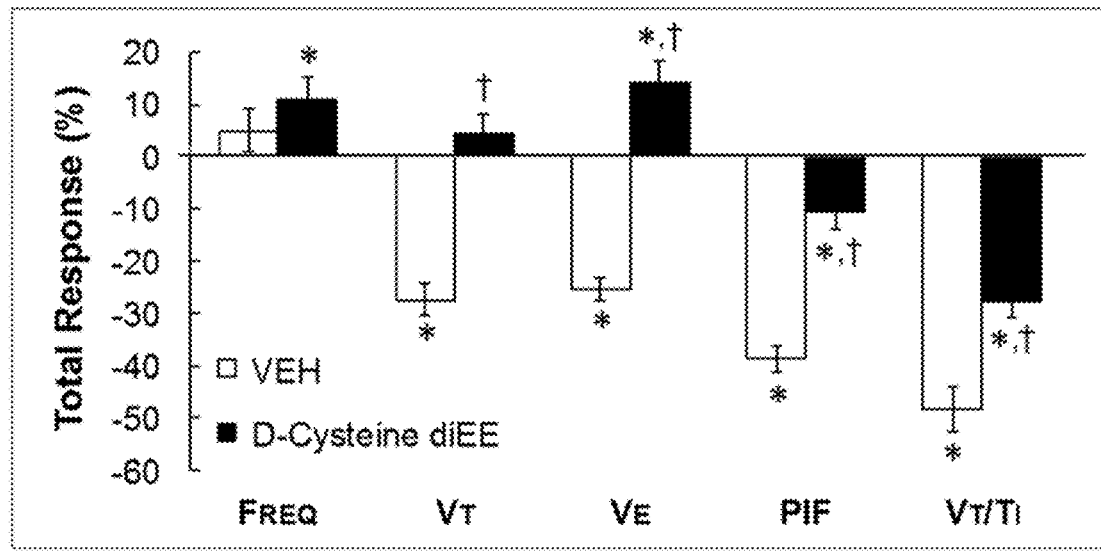
Figure 6A:
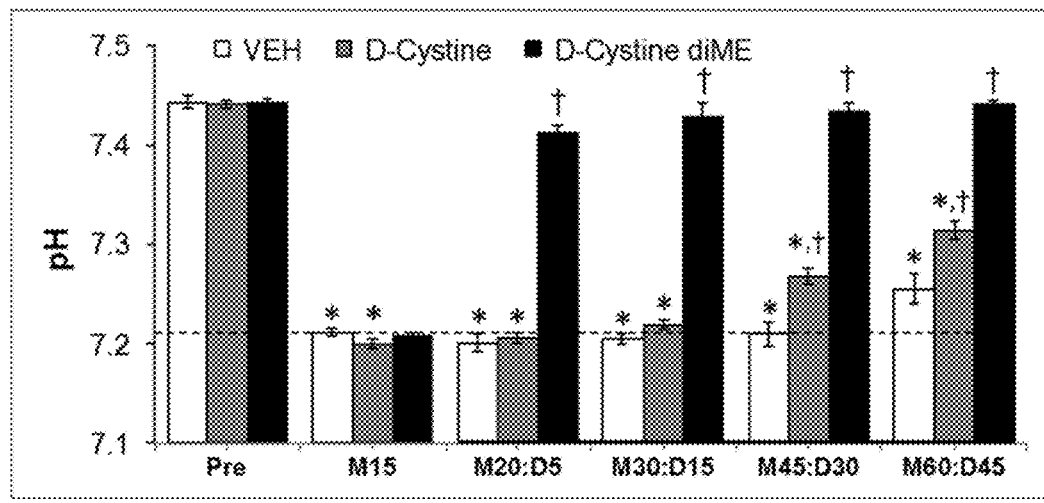
FIGS. 6(A-E) illustrate graphs showing the effects of D-Cystine (500 μmol/kg, i.v.) and D-Cystine diME (500 μmol/kg, i.v.) on arterial blood-gas chemistry and A-a gradients in rats which had previously received a bolus injection of morphine (10 mg/kg, i.v.). Data are mean±SEM (n=9 rats per group). *P<0.05, difference from pre-values. †P<0.05, D-Cystine or D-Cystine diME versus vehicle.
Figure 6B:
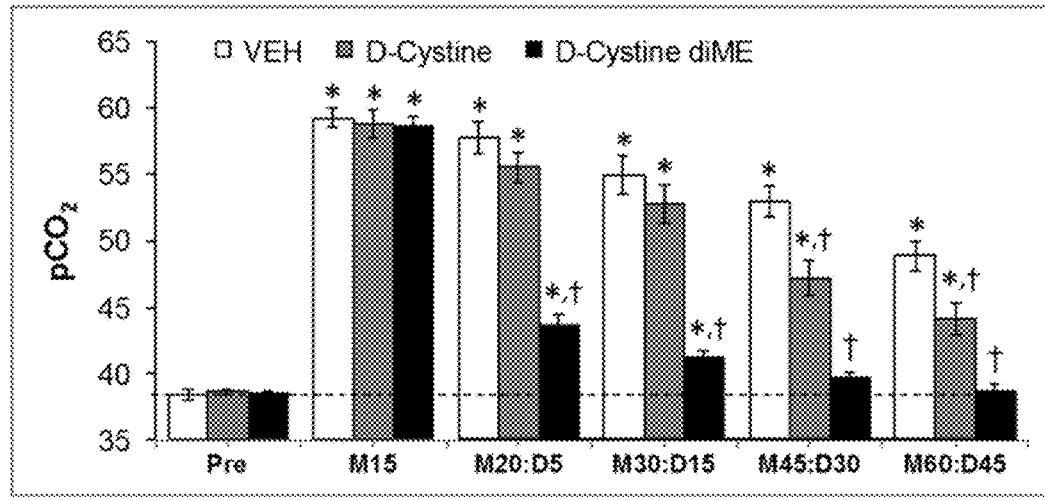
Figure 6C:
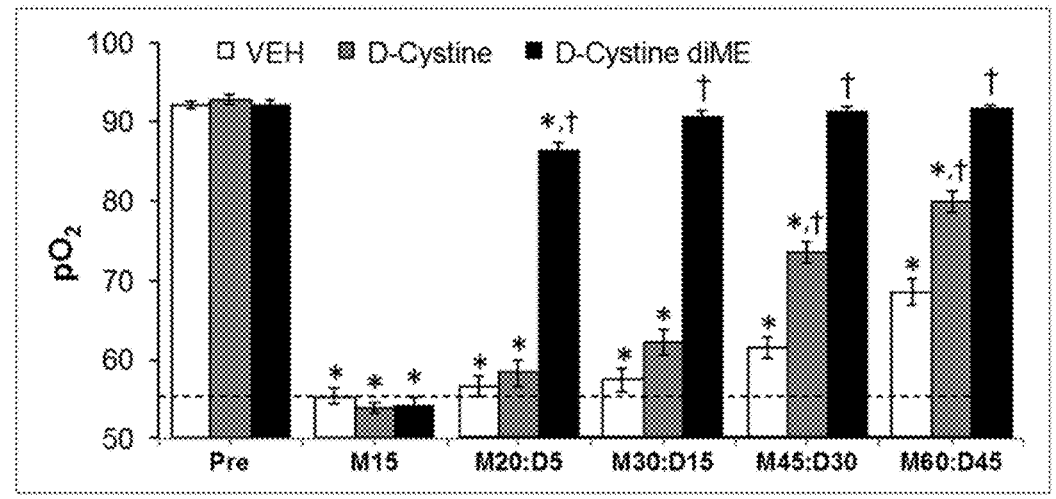
Figure 6D:
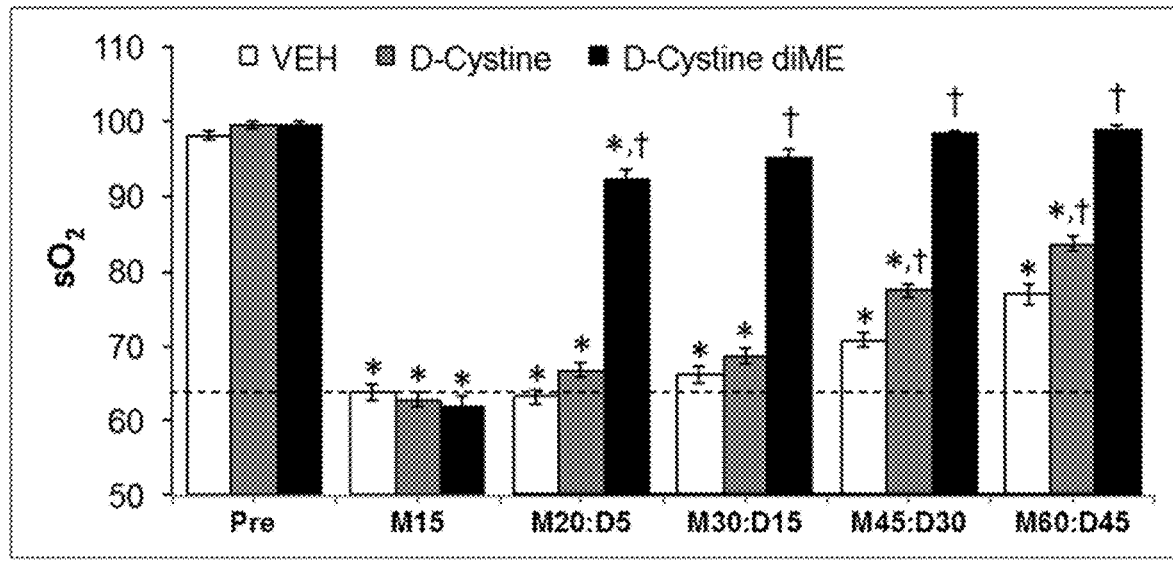
Figure 6E:
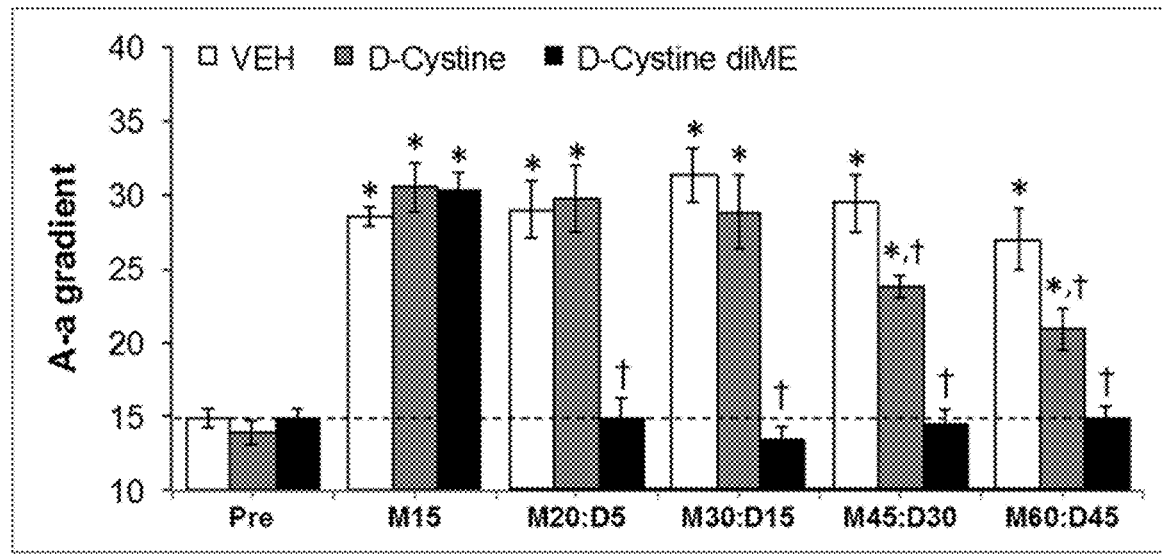

In order to assess whether the responses to D-Cystine diME were unique to rats, we examined the effects of a 250 µmol/kg dose of D-Cystine diME on ventilatory parameters in conscious (adult male) C57 black 6 (C57BL6) mice. As seen in FIG. 4, this dose of D-Cystine diME elicited robust increases in frequency of breathing, tidal volume and minute ventilation of approximately 20 min in duration. The responses were equivalent to those in conscious rats.

D-Cystine diEE and D-Cystine diME Reverse Opioid-Induced Respiratory Depression in Conscious Rats D-Cystine diEE Elicits an Immediate and Sustained Reversal of the Ventilatory Depressant Effects of Morphine As shown in FIG. 5, a bolus injection of D-Cystine diEE (500 µmol/kg, i.v.) elicited an immediate and sustained reversal of the ventilatory depressant effects of morphine (10 mg/kg, i.v.) including the derived parameter, tidal volume/inspiratory time (Vt/Ti), which is an index of central respiratory drive. The dramatic and sustained effect of D-Cystine diEE on tidal volume is a vital effect because the decrease in tidal volume is an integral component of morphine-induced changes in arterial blood-gas (ABG) chemistry (see below).

D-Cystine diME Reverses Morphine's Effects on ABG Chemistry

As shown in FIG. 6, the bolus injection of D-Cystine diME (500 µmol/kg, i.v.) reversed the deleterious actions of morphine (10 mg/kg, i.v.) on ABG chemistry and Alveolar-arterial (A-a) gradient (index of gas-exchange in the lungs). The bolus injection of D-cystine itself (500 µmol/kg, i.v.) elicited minor delayed effects (FIG. 6).

D-CYSee Reverses the Ventilatory Depressant Effects of Morphine

As shown in FIG. 7, the possibility that D-cystine diME exerts its effects via generation of D-Cysteine in cells is supported by findings that injections of D-CYSee (2×500 µmol/kg, i.v.) also elicited a sustained reversal of the effects of morphine (10 mg/kg, i.v.). As with D-Cystine diME, a key feature of D-CYSee is its ability to reverse the effects of morphine on tidal volume.

D-CYSee Reverses Morphine's Effects on ABG Chemistry and A-a Gradient

As seen in FIG. 8, a single injection of D-CYSee (500 µmol/kg, i.v.) elicited a sustained reversal of the deleterious effects of morphine (10 mg/kg, i.v.) on ABG chemistry and A-a gradient. D-cysteine itself (500 µmol/kg, i.v.) elicited minimal effects.

Prior Infusion of L-CYSee Blunts the Ventilatory Depressant Effects of Morphine

Although the ability of bolus injections of D-Cystine diME and D-CYSee to reverse opioid-induced depression of ventilation is of vital importance, it is also important to determine whether prior administration of these compounds can prevent the deleterious actions of opioids. Although we are yet to examine the D-isomers, we have established that prior infusion of L-CYSee (14.3 µmol/kg/min, total dose of 500 µmol/kg, i.v.) over 35 min (1) dramatically increased peak inspiratory flow and respiratory drive (Vt/Ti) in conscious rats, and (2) markedly blunted the subsequent effects of a bolus injection of morphine (10 mg/kg, i.v.). As can be seen, a subsequent injection of L-CYSee (250 µmol/kg/min) elicited prompt beneficial effects in these rats (FIG. 9).

Prior Infusion of L-CYSee but not L-SERee Morphine's Effects on ABG Chemistry and A-a Gradient As seen in FIG. 10, the prior infusion of L-CYSee 14.3 µmol/kg/min, total dose of 500 µmol/kg, i.v. over 35 min) virtually eliminated the deleterious effects of morphine (10 mg/kg, i.v.) on ABG chemistry and A-a gradient. In contrast, the infusion of identical amount of L-SERee was without effect on morphine, again high-lighting the key involvement of the sulfur atom in the beneficial effects of L-CYSee.

Preliminary Toxicology Studies

Hemodynamics

L-CYSee (500 µmol/kg, i.v.) elicited substantial transient decreases in mean arterial blood pressure (MAP) via decreases in cardiac output and heart rate (no changes in total peripheral resistance). In contrast, L-CYSee, and in particular D-Cystine diME, elicited minimal responses (FIG. 11).

Analgesia

Although pretreatment with D-CYSee (500 µmol/kg, i.v.) did not affect the initial level of analgesia (paw withdrawal latency) elicited by morphine (5 mg/kg, i.v.) in conscious rats, the analgesia decayed more quickly (FIG. 12). D-cystine diethyl ester (D-cystine DEE) (500 µmol/kg, i.v.) however does not attenuate morphine analgesia elicited by 10 mg/kg of morphine (dose eliciting depression of breathing in our ventilatory studies) (FIG. 13), suggesting it may be an ideal respiratory stimulant in the setting of narcotic-induced respiratory depression.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A pharmaceutical composition comprising:
a respiratory depressant and an amount of a cystine ester or a pharmaceutically acceptable salt thereof effective to restore ventilatory and/or respiratory drive depressed by the respiratory depressant in a subject; wherein the cystine ester has the formula:

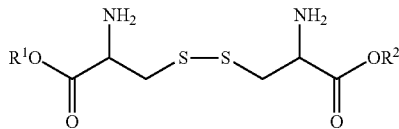

where $R^1$ and $R^2$ are the same or different and are selected from the group consisting of H, unsubstituted or substituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl, and heterocyclyl containing from 5-14 ring atoms, wherein at least one of $R^1$ or $R^2$ is not a H; or pharmaceutically acceptable salts thereof.

2. The composition of claim 1, wherein the respiratory depressant comprises at least one of an anesthetic, a sedative, an anxiolytic agent, alcohol, or a narcotic.

3. The composition of claim 1, wherein the respiratory depressant comprises a narcotic analgesic.

4. The composition of claim 1, wherein the respiratory depressant comprises at least one of an opioid, morphine, fentanyl, oxycodone, or buprenorphine.

5. The composition of claim 1, wherein $R^1$ and $R^2$ are independently H or an unsubstituted or substituted $C_1$-$C_{24}$ alkyl, wherein at least one of $R^1$ or $R^2$ is not a H.

6. The composition of claim 1, wherein $R^1$ and $R^2$ are independently selected from the group consisting of H, methyl, ethyl, propyl, and butyl, wherein at least one of $R^1$ or $R^2$ is not a H.

7. The composition of claim 1, wherein the cystine ester is a cystine dialkyl ester.

8. The composition of claim 7, wherein the cystine dialkyl ester is a D-cystine dialkyl ester or pharmaceutically acceptable salt thereof.

9. The composition of claim 7, wherein the cystine dialkyl ester is selected from the group consisting of cystine dimethyl ester, cystine diethyl ester, combinations thereof, and pharmaceutically acceptable salts thereof.

10. The composition of claim 7, wherein the cystine dialkyl ester is D-cystine dimethyl ester.

11. A composition comprising:
a narcotic analgesic and an amount of a cystine ester or a pharmaceutically acceptable salt thereof effective to restore ventilatory and/or respiratory drive depressed by the narcotic analgesic in a subject; wherein the cystine ester has the formula:

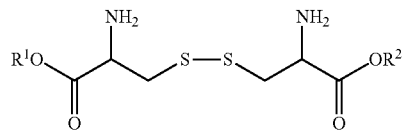

where $R^1$ and $R^2$ are the same or different and are selected from the group consisting of H, unsubstituted or substituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl, and heterocyclyl containing from 5-14 ring atoms, wherein at least one of $R^1$ or $R^2$ is not a H; or pharmaceutically acceptable salts thereof.

12. The composition of claim 11, wherein the narcotic analgesic comprises at least one of an opioid, morphine, fentanyl, oxycodone, or buprenorphine.

13. The composition of claim 11, wherein $R^1$ and $R^2$ are independently H or an unsubstituted or substituted $C_1$-$C_{24}$ alkyl, wherein at least one of $R^1$ or $R^2$ is not a H.

14. The composition of claim 11, wherein $R^1$ and $R^2$ are independently selected from the group consisting of H, methyl, ethyl, propyl, and butyl, wherein at least one of $R^1$ or $R^2$ is not a H.

15. The composition of claim 11, wherein the cystine ester is a cystine dialkyl ester.

16. The composition of claim 15, wherein the cystine dialkyl ester is a D-cystine dialkyl ester or pharmaceutically acceptable salt thereof.

17. The composition of claim 15, wherein the cystine dialkyl ester is selected from the group consisting of cystine dimethyl ester, cystine diethyl ester, combinations thereof, and pharmaceutically acceptable salts thereof.

18. The composition of claim 15, wherein the cystine dialkyl ester is D-cystine dimethyl ester.

* * * * *